United States Patent [19]
Pohlenz et al.

[11] Patent Number: 5,846,803
[45] Date of Patent: Dec. 8, 1998

[54] PROCESS FOR THE ISOLATION AND CHARACTERIZATION OF A GENE ENZYME SYSTEM FOR INACTIVATION OF THE HERBICIDE PHENMEDIPHAM AND TRANSFER OF THE GENE INTO PLANTS TO PRODUCE HERBICIDE-TOLERANT PLANTS

[75] Inventors: Hans-Dieter Pohlenz; Werner Boidol; Wolfgang Streber, all of Berlin, Germany

[73] Assignee: Hoechst Schering AgrEvo GmbH, Berlin, Germany

[21] Appl. No.: 446,934

[22] Filed: May 23, 1995

Related U.S. Application Data

[62] Division of Ser. No. 196,361, Feb. 14, 1994, Pat. No. 5,543,306, which is a division of Ser. No. 615,448, Nov. 19, 1990, Pat. No. 5,347,076, which is a continuation-in-part of Ser. No. 353,871, May 18, 1989, abandoned.

[30] Foreign Application Priority Data

May 19, 1988 [FR] France ..................................... 3817384

[51] Int. Cl.⁶ .............................. C07H 21/04; C07K 1/36; C07K 7/08; C07K 14/00
[52] U.S. Cl. ......................... 435/227; 300/325; 300/326; 435/6; 530/24.32; 530/416; 530/417; 530/420
[58] Field of Search ........................... 530/300, 326–329, 530/350, 412, 416–417, 420, 427, 24.32; 435/6, 227

[56] References Cited

U.S. PATENT DOCUMENTS 4,810,648  3/1989  Stalker ................................ 435/240.1

OTHER PUBLICATIONS

C. O. Knowles et al. "Microbial Degradation of the Carbamate Pesticides Desmedipham, Phenmedipham, Promecarb, and Propamocarb",*Bull. Environm. Contam. Toxicol.*, 27, 529–533 (1981).
David N. Radin et al. "Herbicide–tolerant tobacco mutants selected in situ and recovered via regeneration from cell structure" *Genet. Res. Camb.*, (1978), 32, pp. 85–89.

*Primary Examiner*—Douglas W. Robinson
*Assistant Examiner*—Amy J. Nelson
*Attorney, Agent, or Firm*—Curtis, Morris & Safford P.C.

[57] ABSTRACT

A process for the isolation and characterization of a gene enzyme system for the inactivation of the herbicide phenmedipham, wherein the enzyme is a carbamate hydrolase of *Arthrobacter oxidans*, which is responsible for the cleavage of the carbamate bond between the benzene rings of phenmedipham. This process includes the isolation of the carbamate hydrolase, the identification of the amino acid sequence of two BrCN cleavage peptides of the carbamate hydrolase, the synthesis of oligonucleotides for specific determination of the carbamate hydrolase sequence by hybridization and identification of the coding region, cloning and specifying the nucleotide sequence of the carbamate hydrolase gene from *Arthrobacter oxidans*.

8 Claims, 20 Drawing Sheets

Fig. 7A

```
                     .              .             30              .              .             60
     TCCTTGCCAGTCACGGCACCCCAGCCAACCCGGAAGTGGCACCTGCTCGGGCACATCGGT

.              .             90              .              .            120
     GCGAACGCTTCGTCCTGATTCCGATGCCAACTGCTTGACGGCCGTGACACATATGTAGCA

.              .            150              .              .            180
     TAGTCGCCTAGCATGGACCCGCAGCACACCTGCTGTCGGCTCCCGCGCTATCCCCGACCA

.              .            210              .              .            240
     GCGCCGGTCACGGGTAGTCCTCGTGAGAGGCACCAGAACGACAACGGCGCACTGTCCCGC

.              .            270              .              .            300
     AACACGGCCGTATAACCCCACCGGGGTCCGCGCCCGAGCTAGTTCTGGCTCAACCATAAG
                                                                         S/D
                     .              .            330              .              .            360
     GAGAACCTCGTGATTACCAGACCGATCGCCCACACCACCGCTGGGGACCTCGGCGGTTGC
                  MetIleThrArgProIleAlaHisThrThrAlaGlyAspLeuGlyGlyCys

.              .            390              .              .            420
     CTTGAAGACGGCCTGTACGTGTTCCGAGGAGTGCCGTACGCCGAGCCGCCGGTCGGCGAC
     LeuGluAspGlyLeuTyrValPheArgGlyValProTyrAlaGluProProValGlyAsp

.              .            450              .              .            480
     CTGCGGTGGCGGGCGGCGCGCCCGCACGCCGGCTGGACCGGCGTCCGCGACGCCTCCGCG
     LeuArgTrpArgAlaAlaArgProHisAlaGlyTrpThrGlyValArgAspAlaSerAla

.              .            510              .              .            540
     TATGGTCCCTCGGCGCCGCAACCCGTGGAGCCTGGCGGCTCGCCGATCCTTGGGACACAC
     TyrGlyProSerAlaProGlnProValGluProGlyGlySerProIleLeuGlyThrHis

.              .            570              .              .            600
     GGCGACCCTCCGTTTGACGAGGACTGCCTGACTCTCAATCTTTGGACCCCGAACCTCGAC
     GlyAspProProPheAspGluAspCysLeuThrLeuAsnLeuTrpThrProAsnLeuAsp
```

Fig. 7B

```
                 .          .         630            .          .         660
GGCGGTAGCCGGCCGGTCCTCGTCTGGATCCATGGTGGGGGCCTACTAACCGGCTCGGGA
GlyGlySerArgProValLeuValTrpIleHisGlyGlyGlyLeuLeuThrGlySerGly

.          .         690            .          .         720
AATCTACCTAACTACGCGACCGATACCTTCGCCCGCGACGGCGACTTGGTAGGTATCTCA
AsnLeuProAsnTyrAlaThrAspThrPheAlaArgAspGlyAspLeuValGlyIleSer

.          .         750            .          .         780
ATCAATTACCGGCTCGGGCCTCTTGGATTCCTCGCAGGAATGGGCGACGAGAATGTCTGG
IleAsnTyrArgLeuGlyProLeuGlyPheLeuAlaGlyMetGlyAspGluAsnValTrp

.          .         810            .          .         840
CTCACCGATCAGGTAGAGGCACTGCGCTGGATTGCAGATAACGTTGCTGCCTTCGGTGGA
LeuThrAspGlnValGluAlaLeuArgTrpIleAlaAspAsnValAlaAlaPheGlyGly

.          .         870            .          .         900
GACCCGAACCGGATCACTCTCGTCGGTCAATCAGGCGGGGCATACTCGATCGCAGCGCTC
AspProAsnArgIleThrLeuValGlyGlnSerGlyGlyAlaTyrSerIleAlaAlaLeu

.          .         930            .          .         960
GCCCAACACCCGGTCGCCCCGTCAGCTGTTCCACCGCGCGATCCTACAAAGCCCACCATTC
AlaGlnHisProValAlaArgGlnLeuPheHisArgAlaIleLeuGlnSerProProPhe

.          .         990            .          .        1020
GGGATGCAACCCCATACAGTTGAAGAATCGACGGCAAGGACGAAGGCCCTGGCCCGGCAT
GlyMetGlnProHisThrValGluGluSerThrAlaArgThrLysAlaLeuAlaArgHis

.          .        1050            .          .        1080
CTCGGGCACGATGACATCGAGGCCCTGCGCCATGAGCCGTGGGAGAGGCTGATTCAAGGC
LeuGlyHisAspAspIleGluAlaLeuArgHisGluProTrpGluArgLeuIleGlnGly

.          .        1110            .          .        1140
ACGATAGGCGTCCTGATGGAACACACCAAATTTGGCGAATGGCCCCTGGCATTCTATCCG
ThrIleGlyValLeuMetGluHisThrLysPheGlyGluTrpProLeuAlaPheTyrPro
                                                     Oligo III
```

Fig. 7C

```
                    ·         ·        1170        ·         ·        1200
         GTGTTCGATGAGGCAACGATACCTCGCCATCCGATTGAGTCCATTATCGATTCCGACATC
         ValPheAspGluAlaThrIleProArgHisProIleGluSerIleIleAspSerAspIle

·         ·        1230        ·         ·        1260
         GAAATCATCATCGGCTGGACACGCGACGAGGGCACTTTTCCGTTTGCCTTCGACCCTCAG
         GluIleIleIleGlyTrpThrArgAspGluGlyThrPheProPheAlaPheAspProGln

·         ·        1290        ·         ·        1320
         GTTTCACAGGCGGATCGCGATCAGGTCGAGTCATGGTTGCAGAAGCGTTTCGGAGACCAC
         ValSerGlnAlaAspArgAspGlnValGluSerTrpLeuGlnLysArgPheGlyAspHis

·         ·        1350        ·         ·        1380
         GCCGCCTCGGCCTACGAGGCTCACGCCGGCGACGGAACCAGTCCTTGGACCGTTATCGCC
         AlaAlaSerAlaTyrGluAlaHisAlaGlyAspGlyThrSerProTrpThrValIleAla

·         ·        1410        ·         ·        1440
         AACGTTGTGGGCGACGAGCTCTTTCACAGCGCTGGGTACCGGGTCGCGGACGAACGGGCA
         AsnValValGlyAspGluLeuPheHisSerAlaGlyTyrArgValAlaAspGluArgAla

·         ·        1470        ·         ·        1500
         ACGCGCAGACCGGTACGGGCCTATCAGTTCGACGTAGTCTCGCCCTTGTCGGACGGAGCC
         ThrArgArgProValArgAlaTyrGlnPheAspValValSerProLeuSerAspGlyAla

·         ·        1530        ·         ·        1560
         CTCGGCGCGGTCCACTGCATCGAAATGCCGTTCACATTTGCCAATCTCGACCGTTGGACG
         LeuGlyAlaValHisCysIleGluMetProPheThrPheAlaAsnLeuAspArgTrpThr
                                                   Oligo I & II
                    ·         ·        1590        ·         ·        1620
         GGGAAGCCGTTCGTGGACGGCCTGGATCCAGACGTGGTGGCTCGGGTGACCAACGTGTTG
         GlyLysProPheValAspGlyLeuAspProAspValValAlaArgValThrAsnValLeu ·         ·        1650        ·         ·        1680
         CATCAGGCCTGGATCGCATTCGTCCGAACGGGAGACCCCACGCACGACCAGTTGCCGGTG
         HisGlnAlaTrpIleAlaPheValArgThrGlyAspProThrHisAspGlnLeuProVal
```

Fig. 7D

```
                  .         .         1650           .         .         1680
CATCAGGCCTGGATCGCATTCGTCCGAACGGGAGACCCCACGCACGACCAGTTGCCGGTG
HisGlnAlaTrpIleAlaPheValArgThrGlyAspProThrHisAspGlnLeuProVal

.         .         1710           .         .         1740
TGGCCAACGTTCCGAGCGGACGACCCAGCGGTGTTGGTCGTCGGCGACGAGGGAGCAGAG
TrpProThrPheArgAlaAspAspProAlaValLeuValValGlyAspGluGlyAlaGlu

.         .         1770           .         .         1800
GTGGCGCGGGATCTAGCGCGCCCGGACCACGTCAGCGTTCGGACCCTATGAGGGTCGCGG
ValAlaArgAspLeuAlaArgProAspHisValSerValArgThrLeu

.         .         1830           .         .         1860
GTCGCCGGGGTCTTGAGGCCGGAGGGCCTCGCGTATGCAGTGATTCGTGGATCACCGGCC

AGTT
```

PROCESS FOR THE ISOLATION AND CHARACTERIZATION OF A GENE ENZYME SYSTEM FOR INACTIVATION OF THE HERBICIDE PHENMEDIPHAM AND TRANSFER OF THE GENE INTO PLANTS TO PRODUCE HERBICIDE-TOLERANT PLANTS

This is a division of application Ser. No. 08/196,361, filed Feb. 14, 1994, issued as U.S. Pat. No. 5,543,306, which is a division of application Ser. No. 07/615,448, filed Nov. 19, 1990, issued as U.S. Pat. No. 5,347,076 which is a continuation in part of application Ser. No. 07/353,871, filed on May 18, 1989 now abandoned.

BACKGROUND OF THE INVENTION

1. Field of the Invention

The present invention relates to a process for the isolation and characterization of a gene enzyme system for the inactivation of the herbicide phenmedipham and transfer of the gene into plants to produce herbicide-tolerant plants. The enzyme is a carbamate hydrolase of *Arthrobacter oxidans,* which is responsible for the cleavage of the carbamate bond between the benzene rings of phenmedipham which is the common name for the herbicide methyl 3-m-tolylcarbamoyloxyphenylcarbamate.

2. Description of the Related Art

In practice it is often necessary to use several herbicides or herbicide mixtures to combat various weeds. These problems can be avoided by a biotechnical change to the plant in which resistance to a non-selective herbicide is introduced.

The production of herbicide-tolerant plants is now coming more to the foreground in the plant protection area.

In order to produce herbicide-tolerant plants, it is necessary first to have a process for the isolation and subsequent purification of an enzyme which is able to inactivate a herbicide, e.g., by metabolism, and then to have a process for characterizing the gene enzyme system containing the DNA sequence that codes for the active enzyme. After these steps the DNA sequence of the gene can be transferred into plants.

Such a process for the isolation and subsequent characterization of a gene enzyme system which can inactivate phenmedipham and the transfer of this gene enzyme system into plants was not previously known.

SUMMARY OF THE INVENTION

It has now been found that a carbamate hydrolase can be isolated from some microorganisms, such as *Arthrobacter oxidans,* which is responsible for the hydrolysis of the carbamate bond between the two benzene rings of phenmedipham. The hydrolysis of this bond leads to herbicidally inactive compounds such as methyl 3-hydroxyphenylcarbamate and meta-toluidine, according to the following reaction:

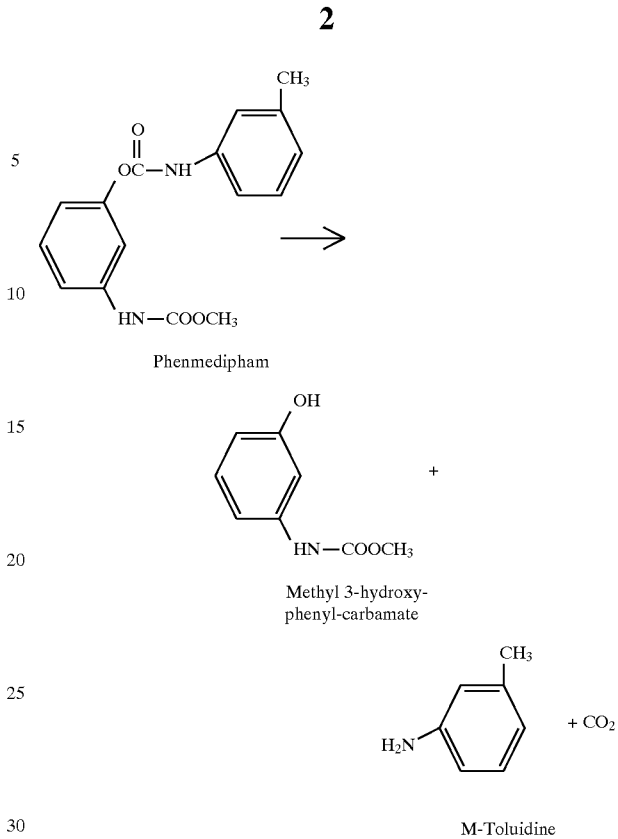

For isolation and subsequent purification of a gene enzyme system which can hydrolyse phenmedipham according to the above described reaction, microorganisms of *Arthrobacter oxidans* are cultivated in a nutrient medium. The carbamate hydrolase responsible for the cleavage of phenmedipham is isolated by ultrasound cell destruction, centrifugation and purification by anion exchange chromatography, gradient elution, ammonium sulfate precipitation and FPLC separation until electrophoretic homogeneity is achieved. From the purified carbamate hydrolase, two peptides are isolated after BrCN cleavage whose sequence can be estimated by Edman degradation. According to the sequence information of these peptides, oligonucleotides can be synthesized which can be used as hybridization probes for the detection of the carbamate hydrolase gene.

In all of the mentioned isolates of the soil bacteria *Arthrobacter oxidans,* plasmids could be detected after lysis of the cells and extraction of the nucleic acids.

For the species *Arthrobacter oxidans* P52, it can be shown that the carbamate hydrolase is coded by one plasmid.

With the loss of the plasmid pHP52 the properties of this species to be able to hydrolytically cleave phenmedipham is lost. Carbamate hydrolysis activity cannot be biochemically established in the plasmid-free derivative of the species P52.

The plasmid pHP52 can be preparatively isolated and mapped with restriction endonucleases. The electrophoretically separated restriction fragments can be transferred onto membrane filters and hybridized with the oligonucleotides. From the data from various blot-hybridizations, it appears that the carbamate hydrolase gene is localized on a PstI restriction fragment with a size of 3.3 kb.

This fragment can be preparatively isolated from the plasmid pHP52 and inserted in the PstI position of the vector pUC19C (Yanish-Perron, C., Vieira, J. & Messing (1985)

Gene 33, 103 ff). After transformation of *E. coli* DH5α with the ligation preparation, two types of recombinant *E. coli* clones are obtained (pp52Pst and pp52Pst inv.) which contain the carbamate hydrolase gene in different orientations to the Lac-promoter of the vector (see FIG. 5).

The carbamate hydrolase can be functionally expressed in the presence of the inducer isopropyl-β-D-thiogalactopyranoside from cultures of the clone of the type *E. coli* DH5a (pp52Pst). In protein extracts of clones of the type *E. coli* DH5α (pp52 inv.) which contain the carbamate hydrolase gene in inverse orientation to the Lac-promoter, no expression of the carbamate hydrolase gene can be detected.

The nucleotide sequence of the carbamate hydrolase gene can be determined according to the method of Sanger et al. (Sanger, F., Niclen, S. & Coulson, A. (1977), Proc. Natl. Acad. Sci, USA 74, 5463–5468).

15 sub-clones arising from the cloning of 3.3 kb long PstI restriction fragments can be constructed in the single strain DNA bacteriophages M13 mp 18 and mp 19 (Messing, J. (1983) Methods in Enzymol, 101, 20–78). In FIG. 6 an extract restriction map of the coded area is represented from which the sequencing strategy can be seen.

The established nucleotide sequence (Seq ID No. 7) with the protein sequence thus derived is illustrated in FIG. 7 (Seq ID No. 6). The amino acid sequences of both established BrCN-splitting peptides (see example 4) can be identified in the same reading frame as the DNA level. This reading frame ends with a TGA translation stop codon (see FIG. 7 (Seq ID No. 6), nucleotide positions 1789–1791) and begins very probably with a GTG-start codon (FIG. 7 (Seq ID No. 6)—nucleotide positions 310–312). Altogether a reading frame of 1479 base pairs results. Upstream of the putative GTG-start codon, a region with significant homology to the consensus sequence for *E. coli* ribosome binding sites ("Shine-Dalgarno Box") can be established (see FIG. 7 (Seq ID No. 6)), nucleotide positions 298–302).

After the nucleotide sequence of the carbamate hydrolase gene has been determined, the construction of plasmids for the expression of carbamate hydrolase in plants can be carried out (see Example 9). For this the chimeric carbamate hydrolase gene on plasmids can be transferred from *E. coli* to *Agrobacterium tumefaciens* and from *Agrobacterium tumefaciens* to the target plants (see Example 10). The operation of the carbamate hydrolase gene in transformed plants can be shown by spraying transformed and untransformed plants with phenmedipham (see Examples 11 and 12).

On the 25th August 1987 the following micro-organisms were deposited at the German Collection of Microorganisms (DSM) in Gottingen, Germany.

| *Arthrobacter oxidans* | P 16/4/B | (DSM 4038) |
| *Arthrobacter oxidans* | P 67 | (DSM 4039) |
| *Arthrobacter oxidans* | P 75 | (DSM 4040) |
| *Arthrobacter oxidans* | P 11/1/–b | (DSM 4041) |
| *Arthrobacter oxidans* | P 15/4/A | (DSM 4045) |
| *Arthrobacter oxidans* | P 21/2 | (DSM 4046) |
| *Arthrobacter oxidans* | P 52, containing the plasmid pHP52 | (DSM 4044). |

Abbreviations

| DEAE | Diethylaminoethyl |
| FPLC | Fast protein/peptide/polynucleotide liquid Chromatography |
| SDS | Sodium lauryl sulfate |
| DTT | Dithiothreitol |
| 1 × SSC | 0.15 M NaCl 0.015 M trisodium citrate pH 7.0 |
| 1 × Denhardt | 0.02% (w/v) Bovine serum albumin (Sigma, Fraction V) 0.02% (w/v) Ficoll 400 0.02% polyvinylpyrroiidone |
| MCS | Multiple cloning site |

Abbreviation for restriction endonucleases
Bm=BamHI, Bs=BstEII, CL=ClaI, EV=EcoRV, HII=HindII, Kp=KpnI, Nc=NcoI, Nd=NdeI, Nh=NheI, Ps=PstI, PvI=PvuI, PvII=PvuII, Sc=SacI, Sp=SphI, St=StuI, Xb=XbaI.

A: Crude extract from the centrifuge supernatant of the ultrasound cell destruction of *Arthrobacter oxidans*.

B: Pooled protein fraction after gradient elution on a DEAE Sephacel column.

C: Ammonium sulfate precipitation of the fraction from B.

D: Protein fraction after gel filtration of the ammonium sulfate precipitation and subsequent separation on a Sephacryl S-300 column.

E: Protein fraction after separation of the pooled fraction from D by FPLC (anion exchange chromatography).

F: Protein fraction after separation of the pooled fraction E on a Superose 6 column (Example 2).

Figure 1:
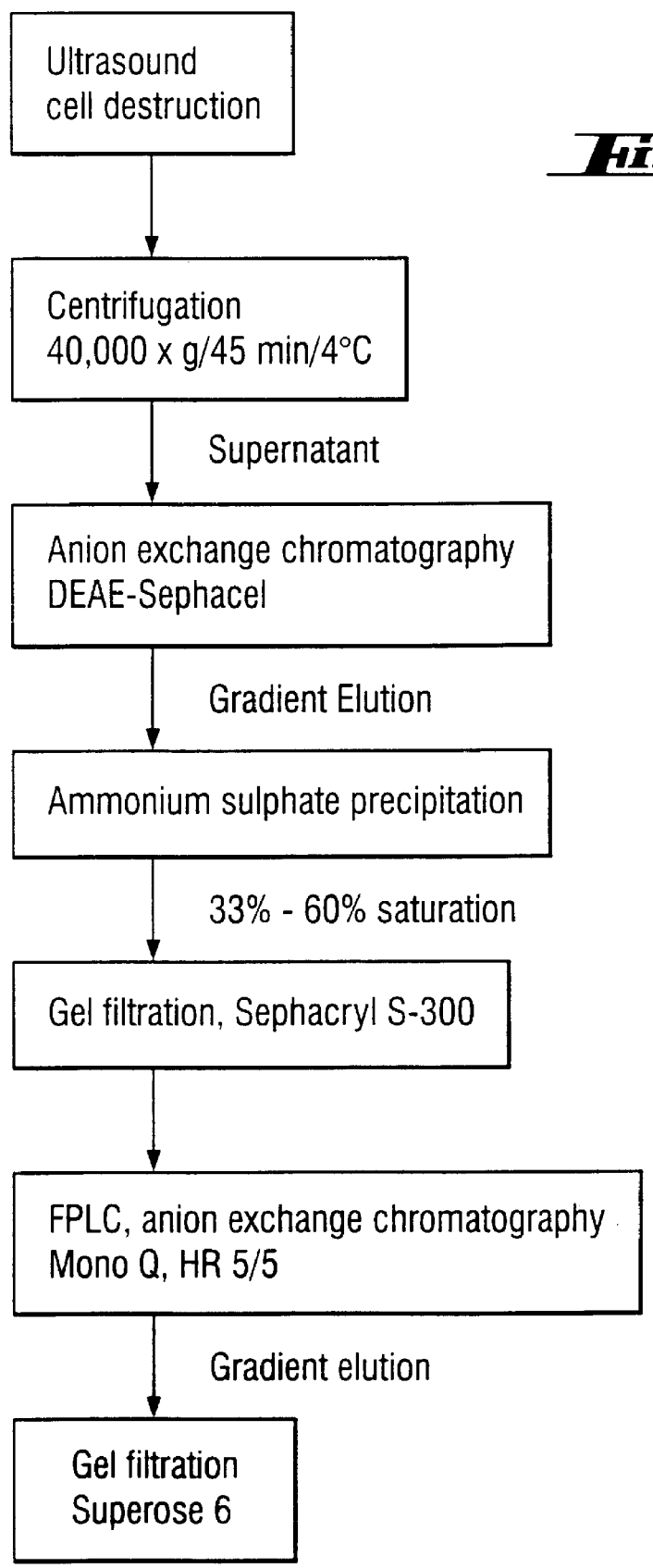
FIG. 1 shows the process for isolating and subsequent purification of phenmedipham cleaving carbamate hydrolase from *Arthrobacter oxidans* (Example 2).
Figure 2:
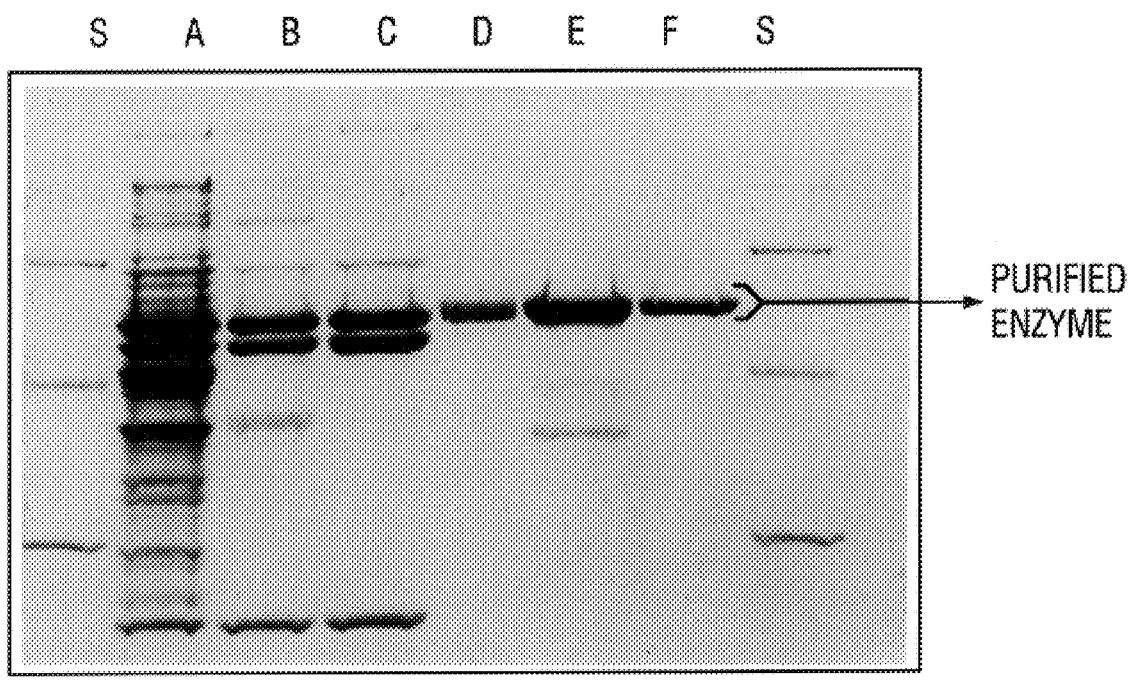
FIG. 2 shows the electrophoretic separation of the crude extract and the isolation and pooled protein fractions after the individual purification steps on an SDS-polyacrylamide gel, in which standard proteins (M) run alongside as markers for the molecular weight.
Figure 3:
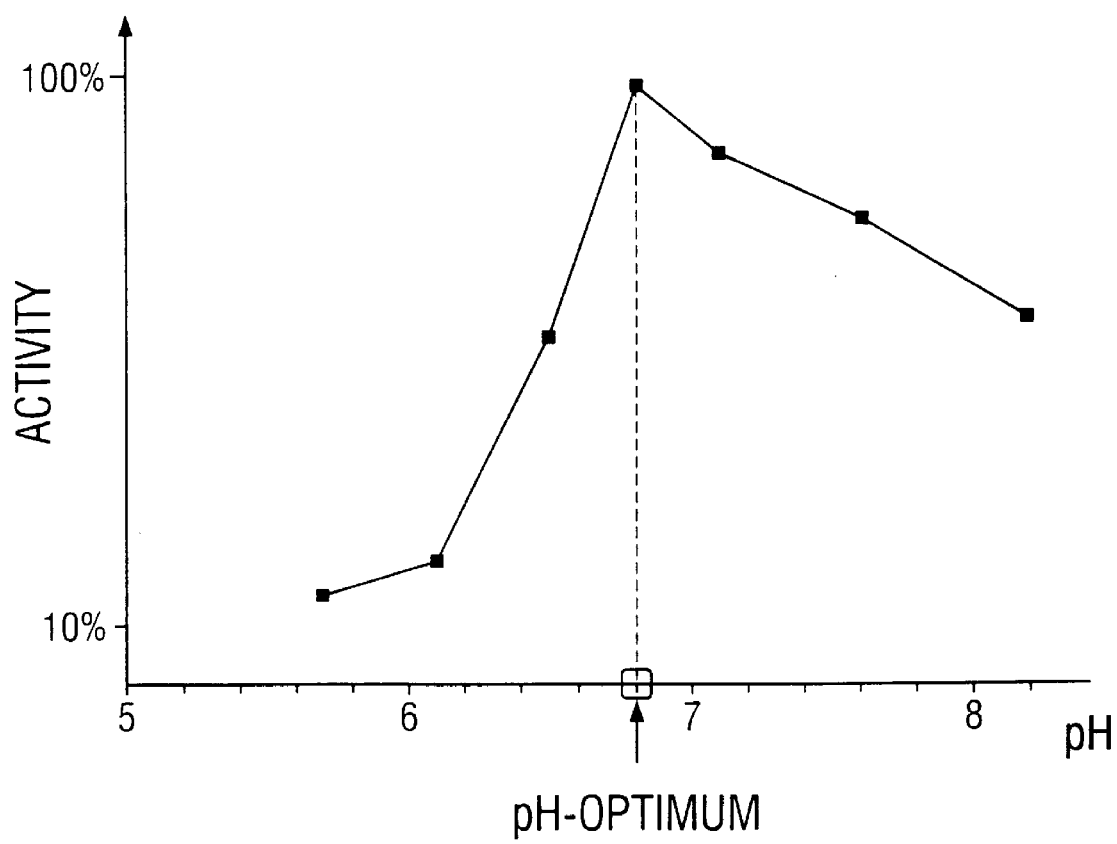

FIG. 3 shows a diagram from which the pH-optimum (pH 6.8) of the carbamate hydrolase can be obtained. The pH optimum can be established in such a way that the enzyme activity as a percentage against the pH value can be derived (Example 2).

Figure 4:
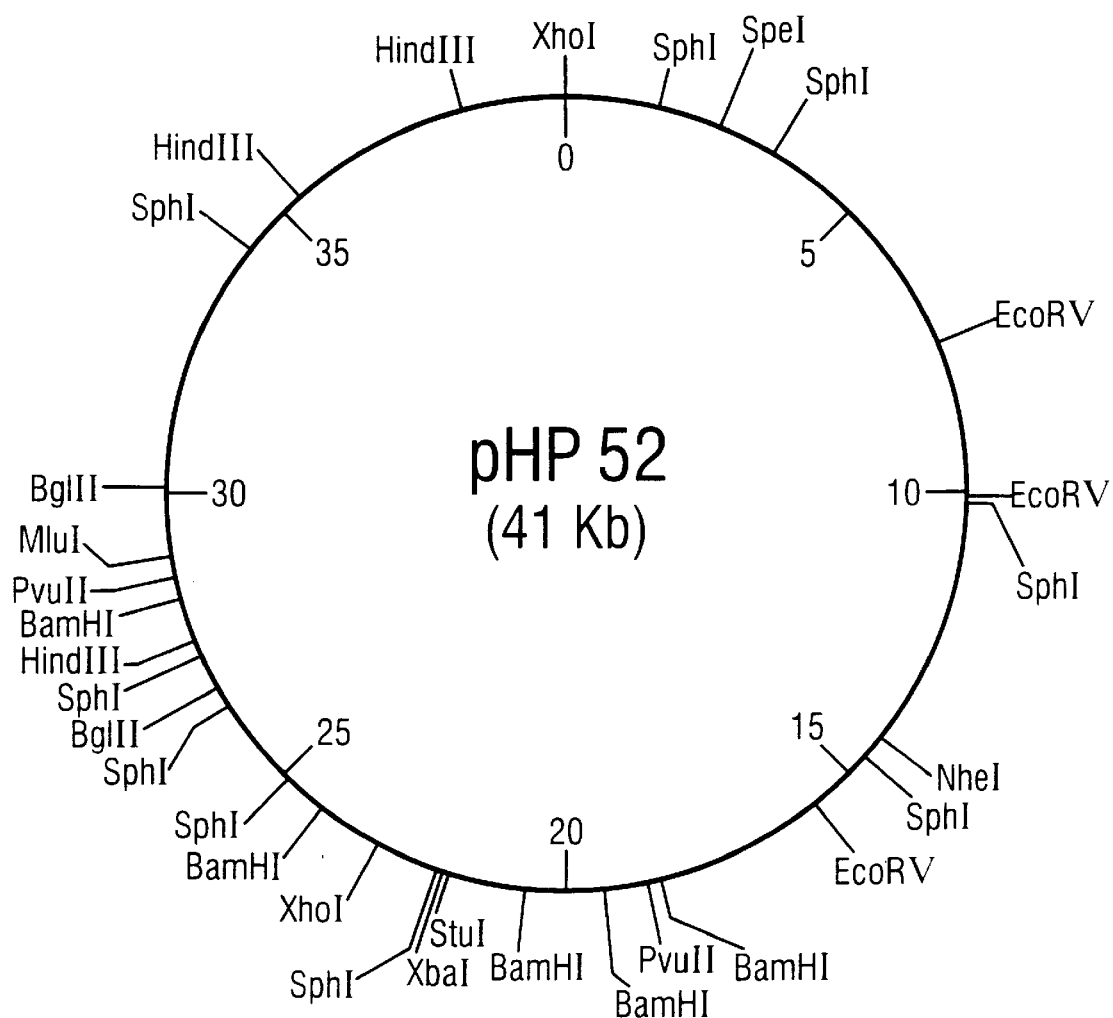

FIG. 4 shows the restriction map of the plasmid pHP52 from the *Arthrobacter oxidans* (species P52).

Figure 5:
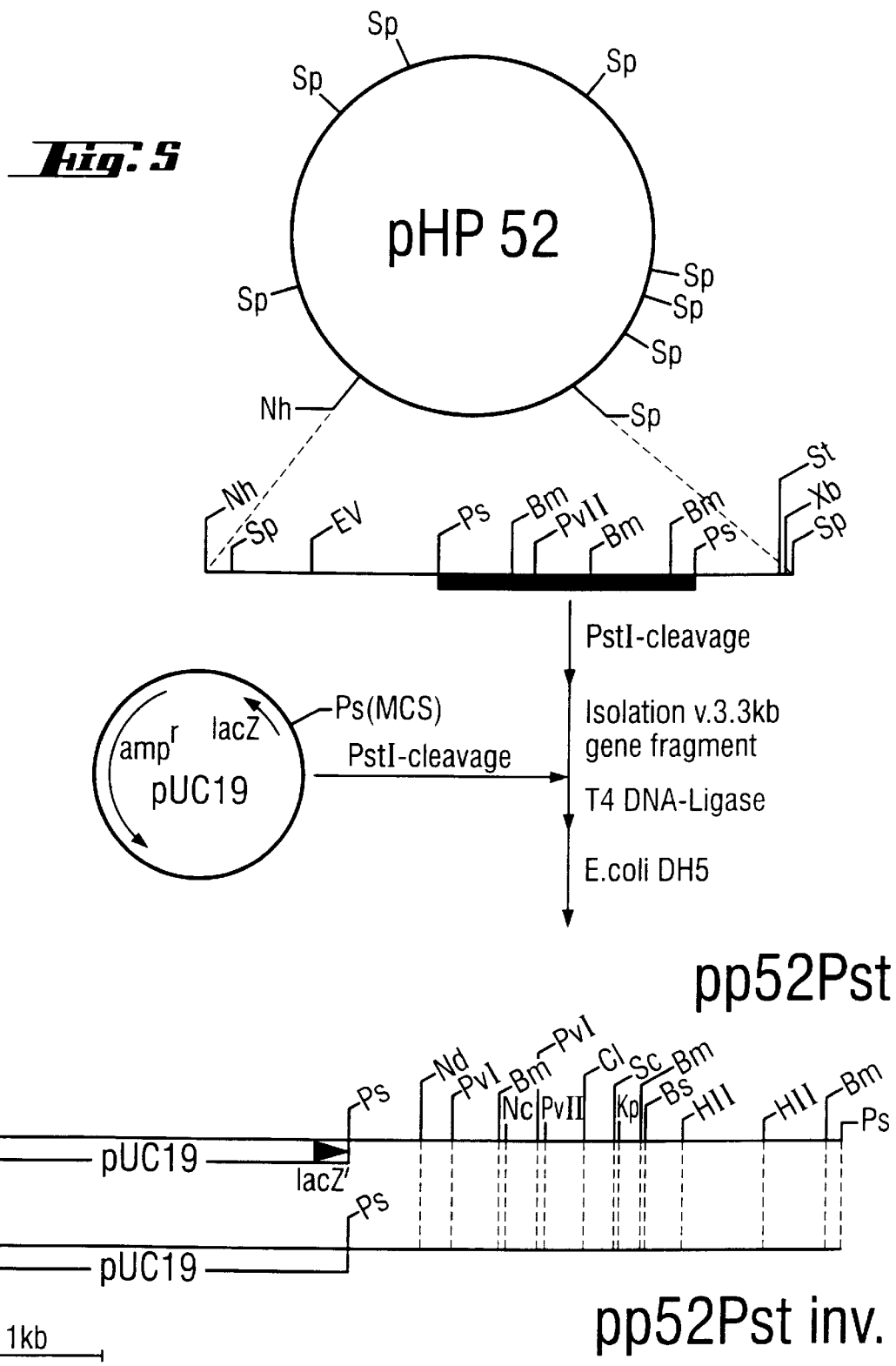

FIG. 5 shows a scheme of cloning of the carbamate hydrolase gene. To improve clarity, the regions of the gene which hybridize with oligonucleotides used, including the 5' and 3' flanking regions are enlarged above the ring-forming plasmid map.

The recombinant clones pp52Pst and pp52Pst inv. are represented in a linear manner. The transcription direction of the lac Z gene is represented by an arrow (▶).

Figure 6:
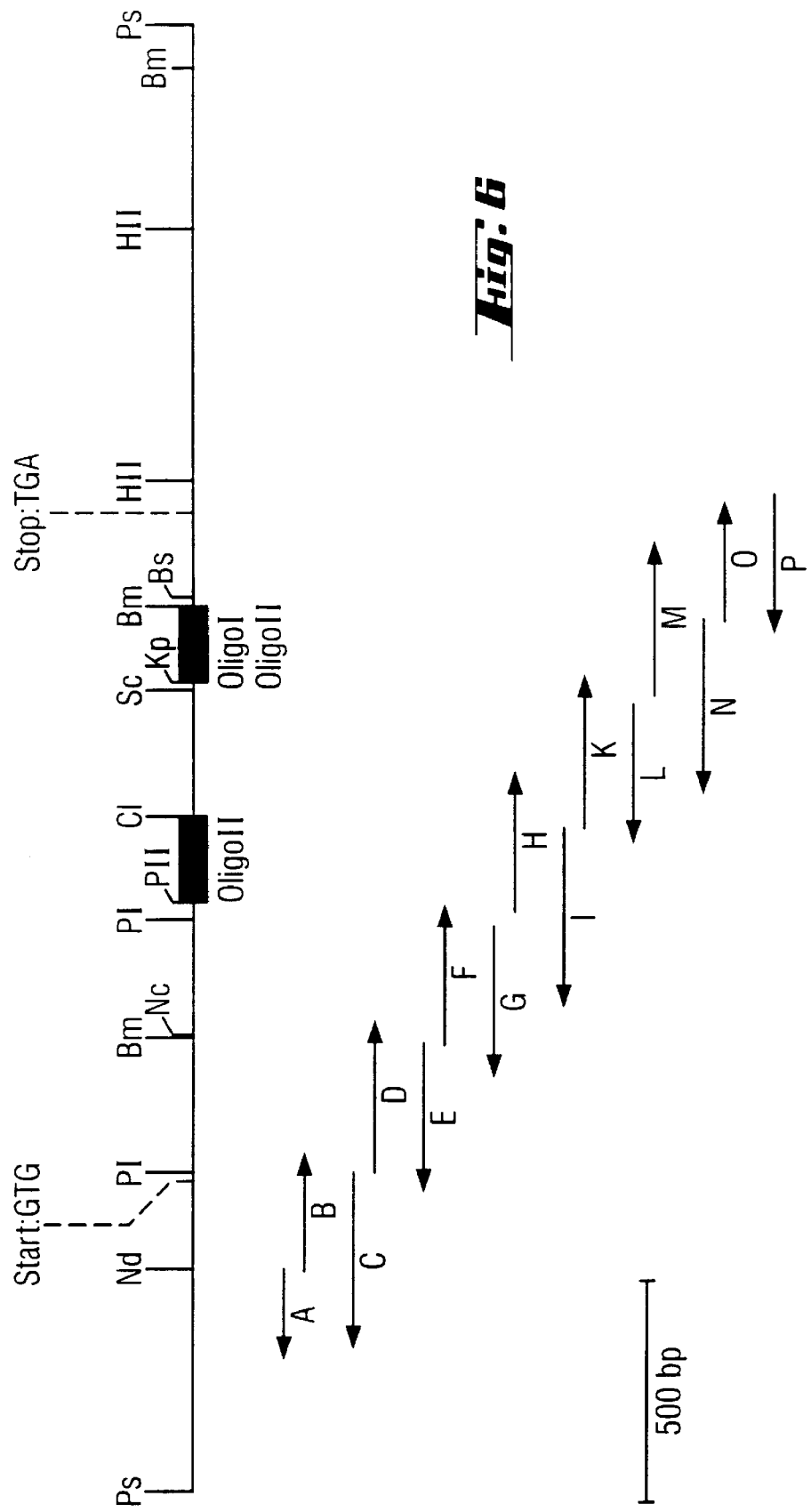

FIG. 6 shows the restriction map of the cloned 3.3 kb PstI restriction fragment which arises from the exact position of the carbamate hydrolase gene (Start: GTG=Start codon, Stop: TGA=Stop codon).

The sequence areas are characterized by arrows under the restriction map. From the length of the arrow can be read the length of the individual sequenced areas.

The restriction fragments which contain the homology areas of the oligonucleotides described in Example 4 are emphasized in the map (—■—).

The M13 clones are described as follows:

| Clone | Inserted Fragment | | M13 Vector |
|---|---|---|---|
| A | HdeI/SacI | (puC18) ~ 500 | mp 18 |
| B | HdeI/SacI | 1289 bp | mp 18 |
| C | PvuI/PstI | ~ 700 bp | mp 19 |
| D | PvuI/PvuI | 564 bp | mp 18 |
| E | BamHI/BamHI | (pUC 19) ~1060 bp | mp 18 |
| F | BamHI/BamHI | 958 bp | mp 18 |
| G | PvuI/PvuI | 564 bp | mp 18 |
| H | PvuII/SacI | 476 bp | mp 18 |
| I | ClaI/BamHI | 561 bp | mp 18 |
| K | ClaI/BamHI | 397 bp | mp 18 |
| L | PvuII/SacI | 476 bp | mp 19 |
| M | KpnI/HindII | 445 bp | mp 19 |
| N | BamHI/BamHI | 958 bp | mp 18 |
| O | BamHI/BamHI | 1100 bp | mp 18 |
| P | KPnI/HindII | 445 bp | mp 18 |

FIGS. 7A to 7D (Seq ID No. 6) shows the nucleotide sequence of the carbamate hydrolase gene including the 5' and 3' flanking area.
Particularly characterized are:
1. The GTG start codon
2. The ribosomal binding site (Shine/Dalgarno Box: S/D)
3. The homology area of the oligonucleotide described in Example 4 (oligo I and II/oligo III).

The coding nucleotide sequence was formally translated as an amino acid sequence. The reading frame is determined clearly by the protein level of the established amino acid partial sequences.

Figure 8:
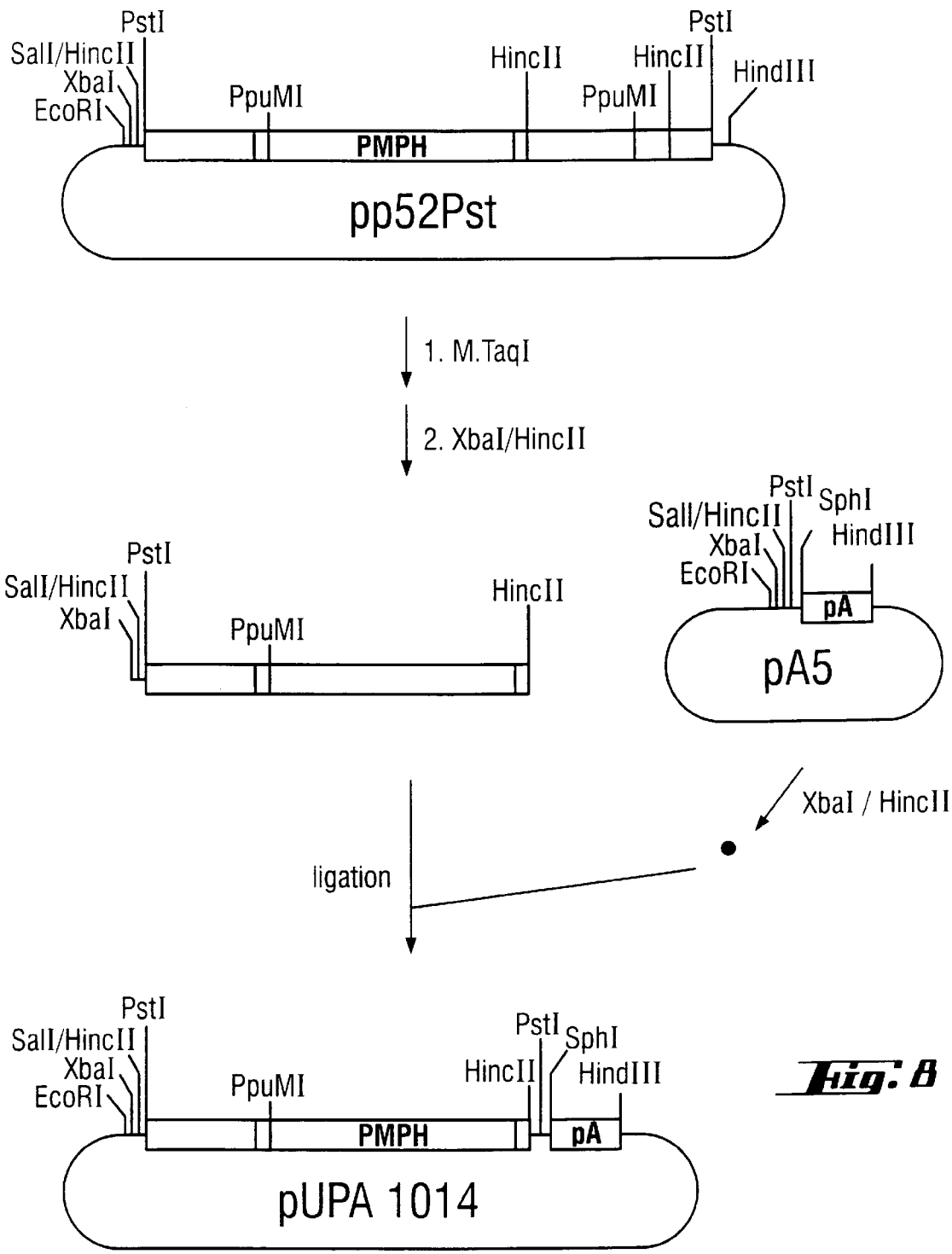

FIG. 8 shows the construction of plasmid pUPA1014. Starting from a 3.3 kb PstI fragment that originates from plasmid pHP52 (example 7) and contains the complete bacterial gene for phenmedipham carbamate hydrolase (PMPH), the untranslated 3'-region of the fragment is replaced by 0.2 kb fragment from the *Agrobacterium tumefaciens* T-DNA containing the octopine synthase gene (OCS) polyadenylation signal (pA). The vectors used are pUC19 (for pp52Pst) and pUC18 (for pA5 and pUPA1014).

Figure 9:
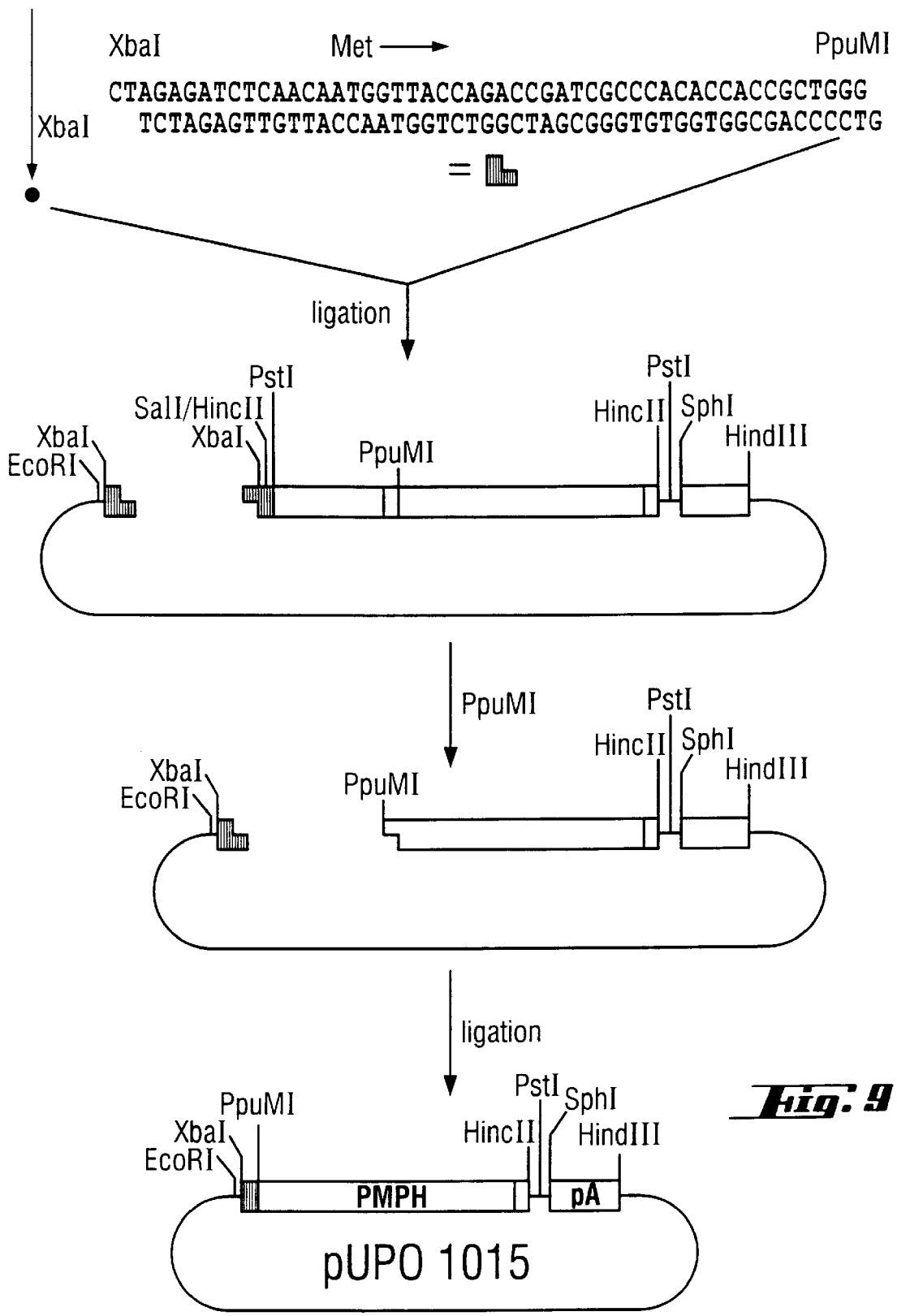

FIG. 9 shows the construction of plasmid pUP01015. In this cloning step the untranslated 5'-region and the N-terminal part of the coding region is removed from the carbamate hydrolase gene and replaced by a synthetic double-stranded oligonucleotide, which reconstitutes the sequence coding for the N-terminal part of the protein. The sequence surrounding the translational start codon is optimal for plant gene expression according to Lutcke et al. EMBO J. 6:43–48, 1987.

Figure 10:
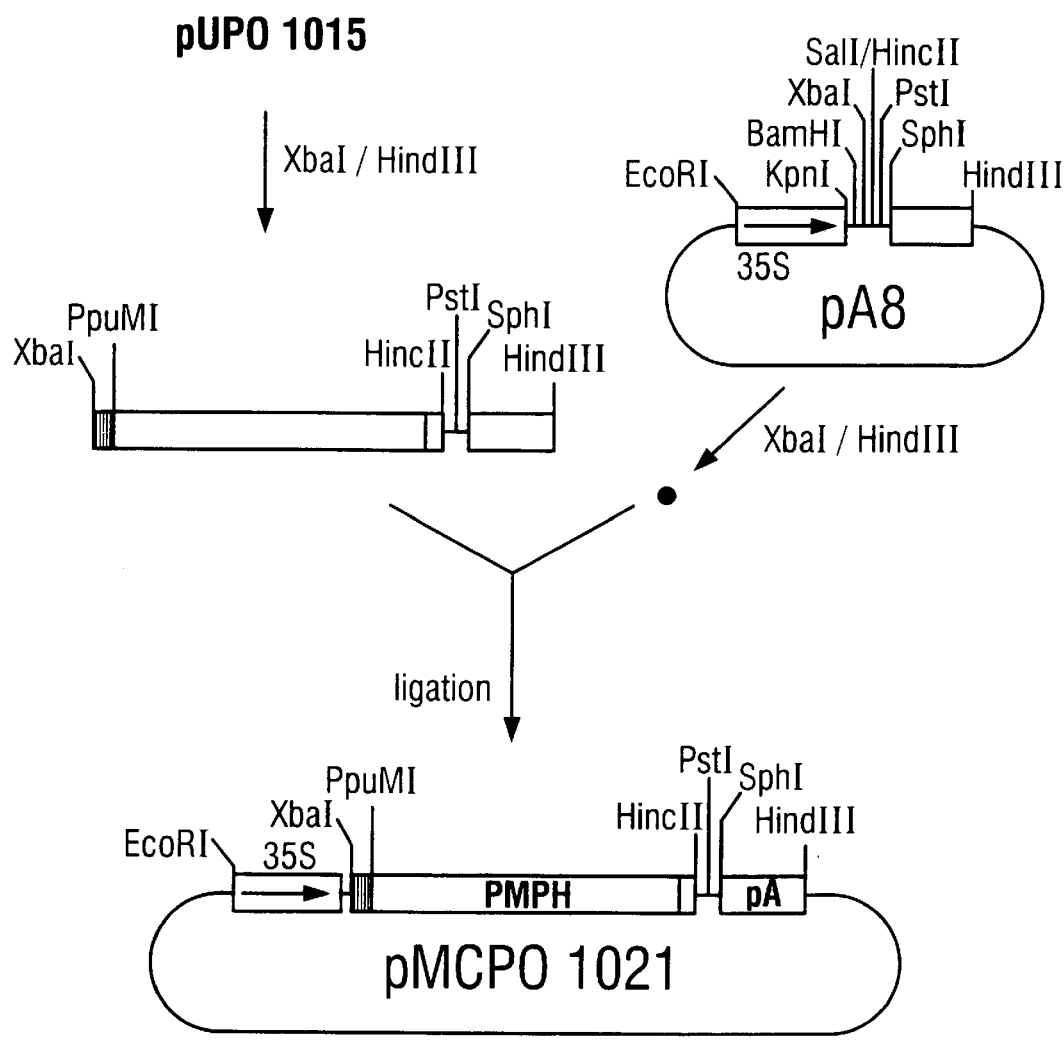

FIG. 10 shows the construction of plasmid pMCP01021. In this cloning step, the coding sequence of the recombinant carbamate hydrolase gene is linked at its 5'-end to the cauliflower mosaic virus (CaMV) 35S promoter contained in plasmid pA8.

Figure 11:
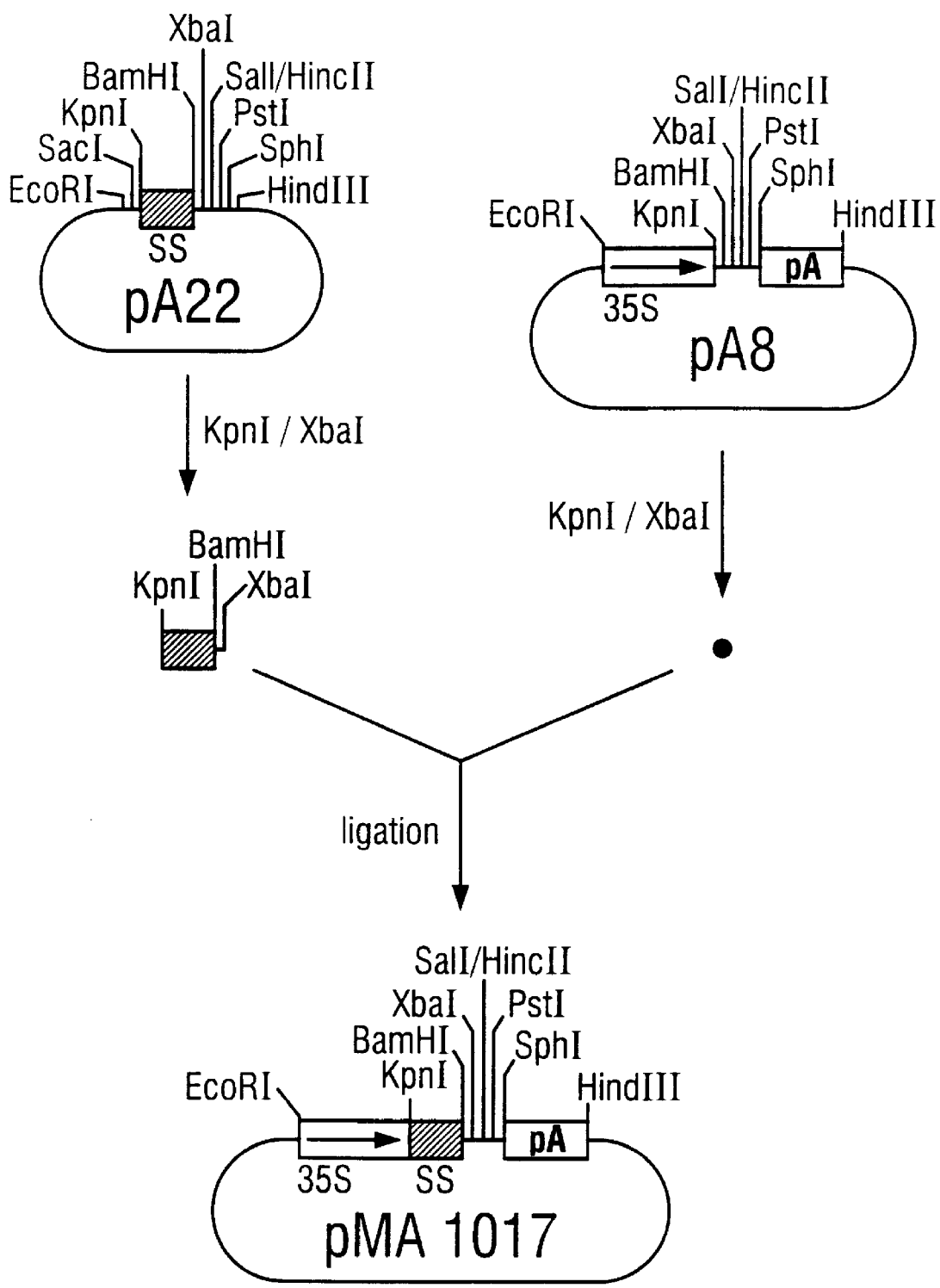

FIG. 11 shows the construction of plasmid pMA1017. In this cloning step a fragment containing the sequence that codes for the potato proteinase inhibitor II signal peptide is inserted in correct orientation between the CaMV 35S promoter and the OCS polyadenylation signal of plasmid pA8 to create an expression vector for targeting introduced genes into the endoplasmic reticulum of plant cells.

Figure 12:
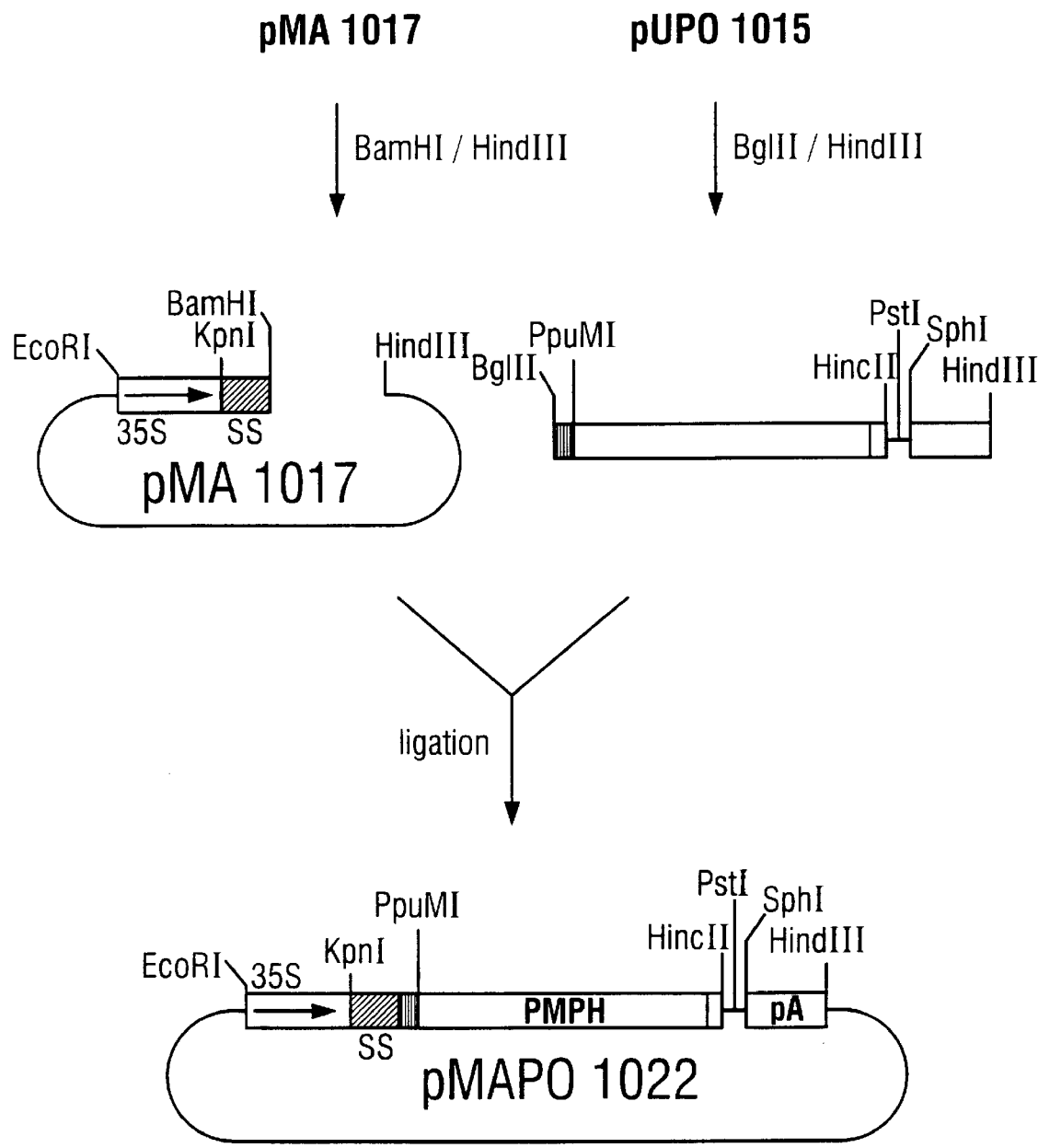

FIG. 12 shows the construction of plasmid pMAP01022. In this cloning step the coding sequence of the recombinant carbamate hydrolase gene is linked at its 5'-end in the correct reading frame to the signal peptide sequence contained in plasmid pMA1017.

Figure 13A:
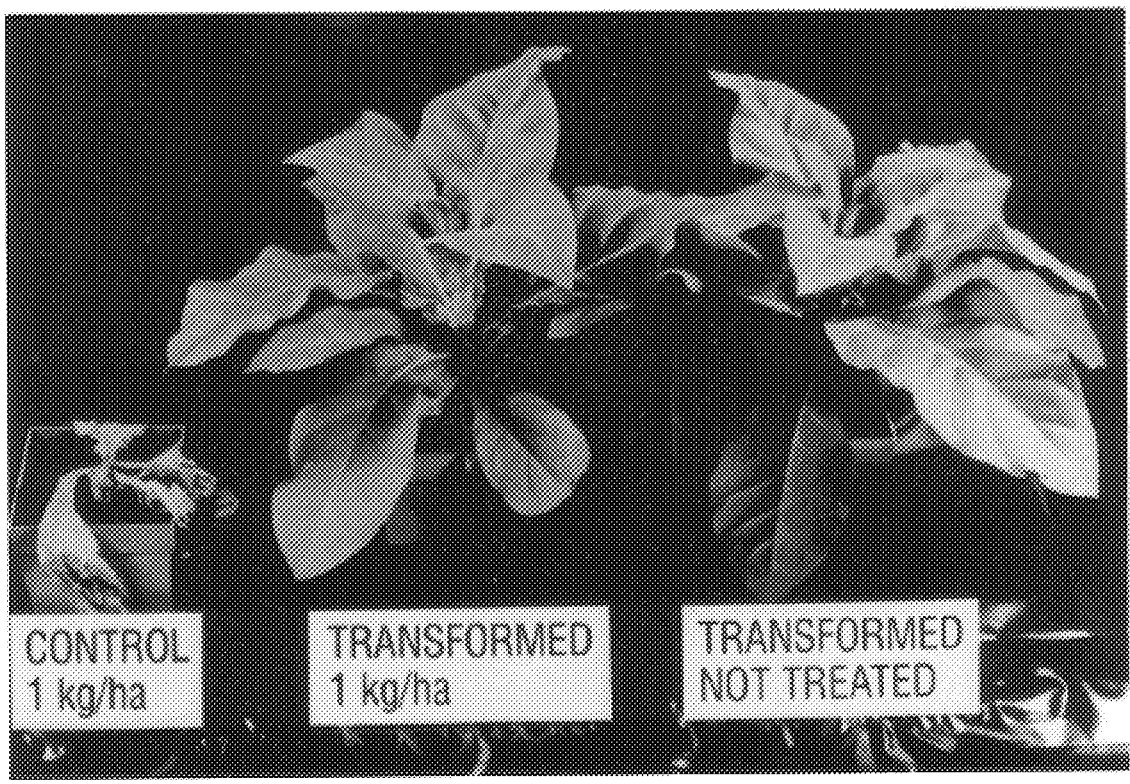
Figure 13B:
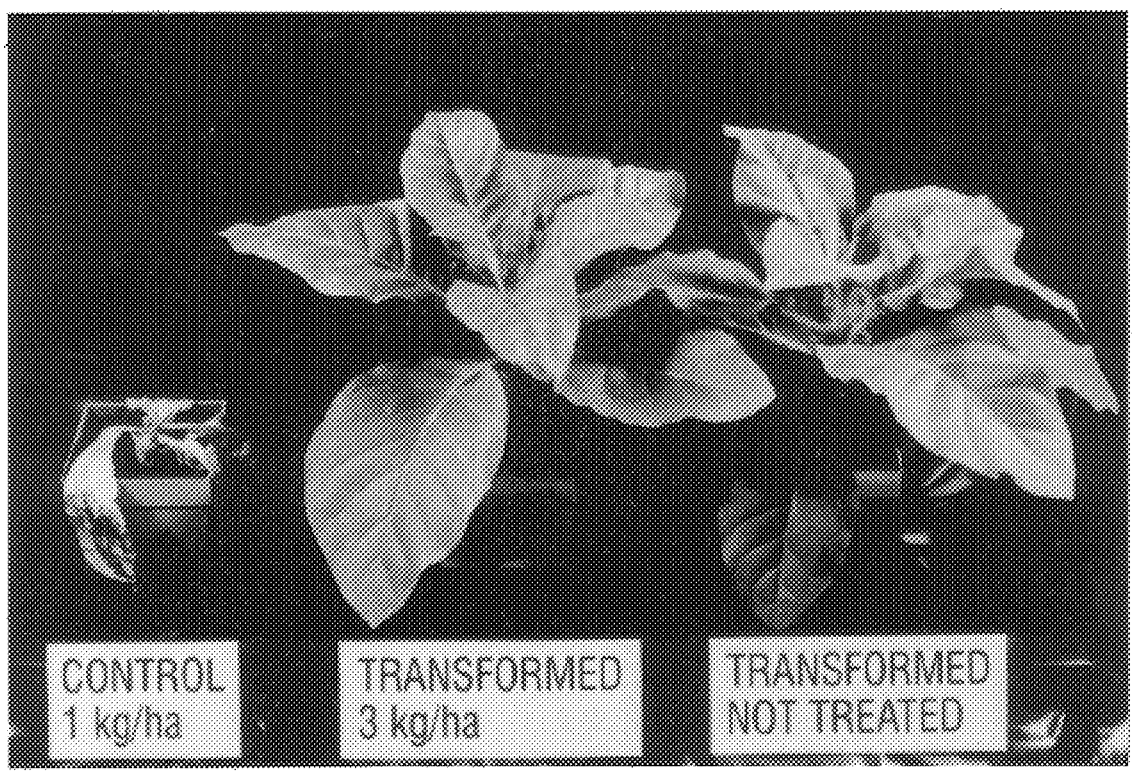
Figure 13C:
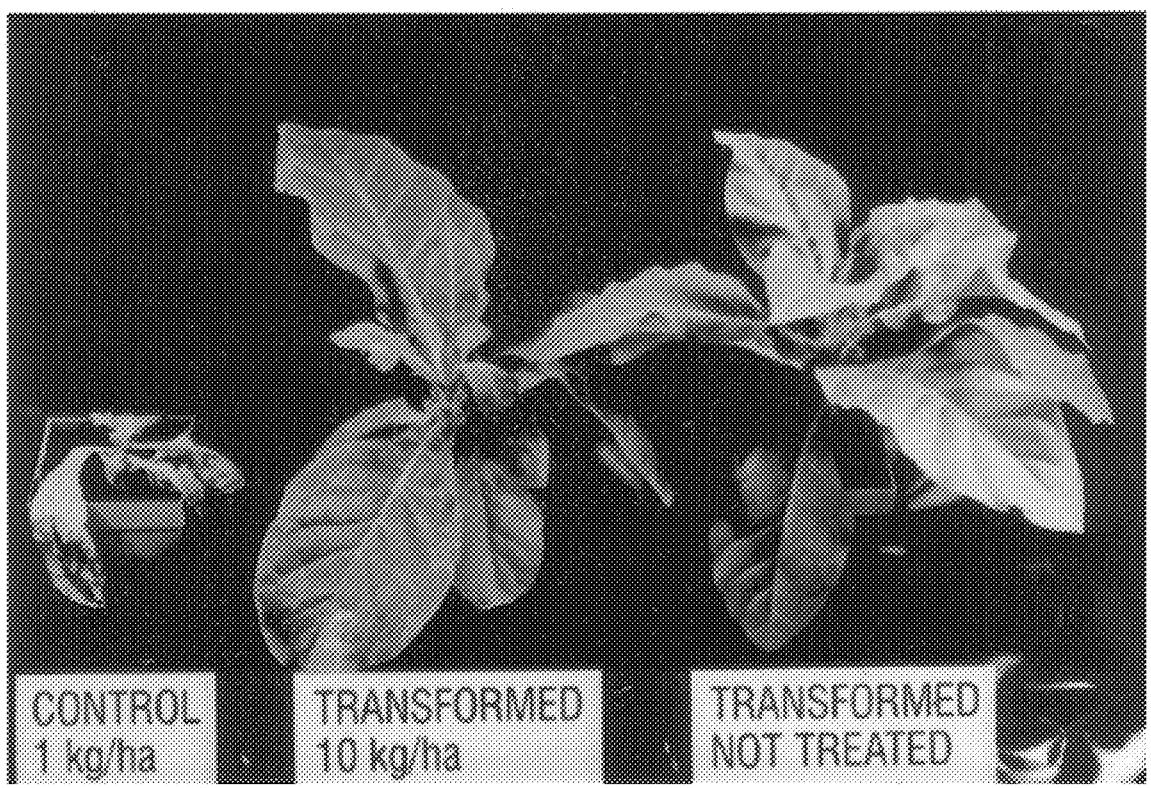

FIGS. 13A to 13C show transgenic tobacco plants WS28-19 in comparison with untransformed control tobacco W38 three weeks after treatment with the herbicide phenmedipham. Photographs A, B, C, show control plants (left) which were sprayed with 1 kg/ha, transgenic plants (middle) which were sprayed with 1 kg/ha (A), 3 kg/ha (B) and 10 kg/ha (C) or transgenic plants (right) which were not treated.

Figure 14:
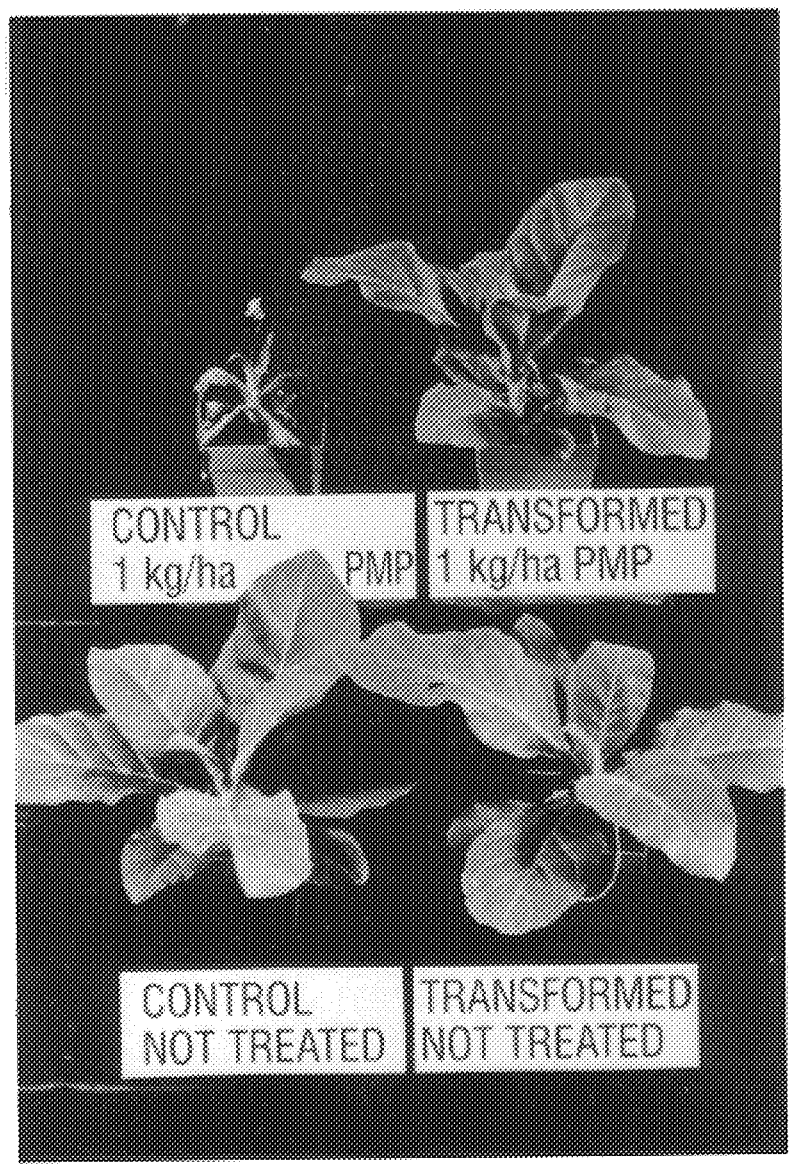

FIG. 14 shows transgenic tobacco plants WS28-19 in comparison with untransformed control tobacco W38 three weeks after treatment with the herbicide phenmedipham. The photograph in FIG. 14 shows untransformed control plants (left) and transgenic plants (right) which were treated with 1 kg/ha phenmedipham (upper row), or left untreated (lower row), respectively.

Figure 15:
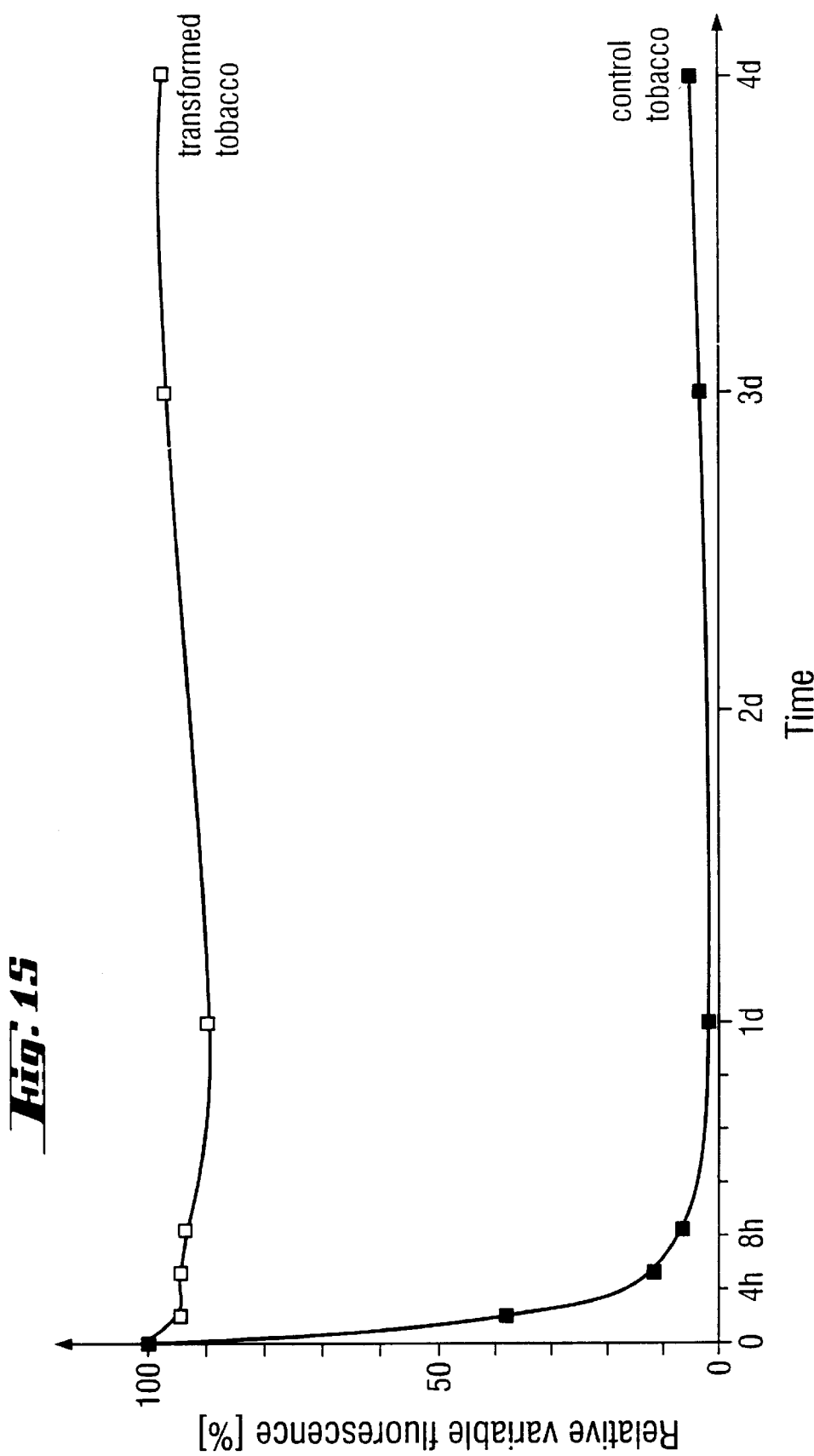

FIG. 15 shows the relative variable fluorescence of intact leaves from a control W38 plant and a transgenic plant WS28-19 after treatment with 1 kg/ha phenmedipham. Measurements were made at indicated intervals after spraying (t=0) as described in the text. Between measurements plants were further incubated in the growth chamber under 16 hours light and 8 hours dark.

DETAILED DESCRIPTION OF THE INVENTION

EXAMPLE 1

Isolation of microorganisms that possess the ability to inactivate the herbicide phenmedipham.

To identify microorganisms which possessed the ability to inactivate the herbicide phenmedipham by metabolism, various microorganisms were screened. As source for the microorganisms, soil samples from various locations (field test sites which had been treated several times with phenmedipham), and also from settling sediment, were used. Selection criteria for the identification of microorganisms which can carry out a carbamate cleavage, were as follows.

a) Growth in a nutrient medium with phenmedipham as a single carbon or nitrogen source.

b) Breaking down of phenmedipham to highly water soluble compounds according to the following reaction.

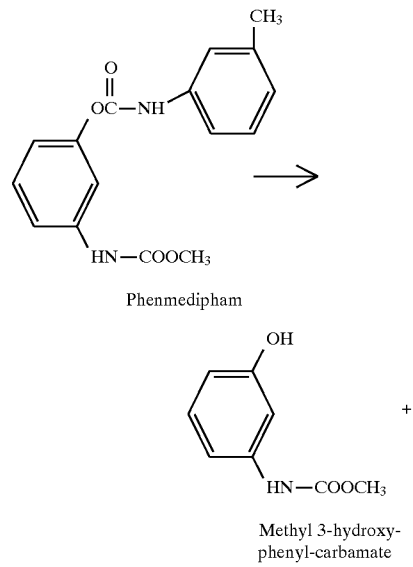

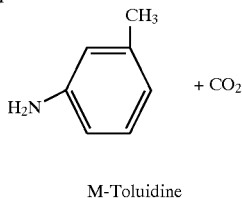

M-Toluidine

From the large number of microorganisms obtained from the soil samples, which were capable of cleavage of phenmedipham, seven representatives were chosen which clearly showed a breakdown. These soil bacteria which are all representatives of the Arthrobacter species and within this species, the sub-species of oxidans, were cultivated in culture broths containing a synthetic medium (M9-medium) having the following composition:

1.0 g/l $NH_4Cl$ 0.25 g/l $MgSO_4.7H_2O$ 3.0 g/l $KH_2PO_4$ 7.0 g/l $Na_2HPO_4.2H_2O$ 2.0 g/l Glucose and 0.5 g/l NACl.

The M9 medium, in addition, contained 1 mg/l thiamine (vitamin B1) as well as trace elements which were added in the form of a stock solution (1 ml/l M9-medium). The trace element stock solution contained:

0.5 Boric acid 0.04 g/l $CuSO_4.5H_2O$ 0.2 g/l $FeCl_3.6H_2O$ 0.4 g/l $MnSO_4.7H_2O$ 0.4 g/l $ZnCl_2$ 0.2 g/l $(NH_4)_6Mo_7O_{24}.4H_2O$ For shaking cultures in liquid mediums, the synthetic medium was supplemented by 0.1% casamino acids (Difco®).

The soil bacteria were incubated in this M9 medium at 28° C. with good aeration until the end of the logarithmic growth phase. For enzyme purification, a total of 10 liters of medium were inoculated with a stationary pre-culture (1:100).

By HPLC analysis of the culture broth it was shown that in the cultures of *Arthrobacter oxidans,* the desired cleavage of phenmedipham to the herbicidally inactive products was achieved.

EXAMPLE 2

Isolation and purification of the carbamate hydrolase from *Arthrobacter oxidans.*

The isolation and subsequent purification of the carbamate hydrolase to electrophoretic homogeneity was carried out over a six stage purification process. From 6 liters of an end logarithmic culture of *Arthrobacter oxidans* (pHP52) (DSM No. 4044), 0.5–1 mg carbamate hydrolase was reproducibly isolated. For isolation of the carbamate hydrolase, the cells were harvested by centrifugation (7000×g) and resuspended in about 40 ml of decomposition buffer (10 mM sodium phosphate pH 6.8/1 mM DTT). The cell suspension was disrupted by ultrasound and homogenized at the same time. The homogenate was then centrifuged for 45 minutes at 40000×g, at 4° C. The sediment was removed and the supernatant, equilibrated with 100 mM Tris-HCl pH 7.2/100 mM NaCl/1 mM DTT, was applied to a DEAE Sephacel column (column diameter 2.6 mm, height of the gel bed 20.5 cm, column volume about 100 ml). Before application to the column, the cell extract was diluted at a ratio of about 1:10 with starting buffer (100 mM Tris/100 mM NaCl/1 mM DTT). The column was then washed with starting buffer in order to remove the unbound material. The carbamate hydrolase was then eluted with a linear gradient 100 mM NaCl–500 mM NaCl (5×column volume). The enzymatically active fractions were pooled and treated with dry ammonium sulfate $(NH_4)_2SO_4$ to an end concentration of 33% of the saturated solution. The resulting protein precipitate was sedimented by centrifugation (20000×g/30 mins) and discarded. The supernatant was treated with solid ammonium sulfate to an end concentration of 60% of the saturated solution and stirred for about 12 hours at 0° C. The sedimented protein was collected by centrifugation (20000×g /30 mins) and dissolved in about 1 ml starting buffer, treated with 10% (w/v) saccharose and loaded to a Sephacryl S-300 column. The gel filtration was carried out at a flow rate of 2.5 cm/h (elution buffer -: start buffer). The column had a diameter of 2.6 cm, a height of 95 cm and a volume of 475 ml. The enzymatically active fraction was then worked up on an FPLC column (mono Q HR 5/5: anion exchange). Gradient elution 100 mM NaCl -: 300 mM NaCl; flow rate: 0.5 ml/mm; application volume 2 ml). The unbound protein was separated by isocratic elution with 19 ml starting buffer. (Gradient elution 100 mM NaCl -: 300 mM NaCl in 20 ml with 100 mM Tris/HCl pH 7.2/1 mM DTT).

The enzymatically active fractions were concentrated by ultra-filtration after electrophoretic analysis of the purity (SDS-polyacrylamide-gel electrophoresis by the method of Lammli), using an Amicon®, Centrikon 10 concentrator, and put on a FPLC gel-filtration column (Superose 6-HR 10/30, Pharmacia) (flow rate 0.2 ml/min: application volume 100 ul: eluent: 100 mM Tris/HCl pH 7.2/10 mM NaCl).

The active protein fractions which result from this step are electrophoretically homogenous.

The isolated enzyme is active in buffered solutions (i.e., buffers conventionally used in biochemical systems, such as phosphate buffers, Tris buffers, etc; pH 6.8). Co-factors or metal ions are not necessary for the reaction. A sensitivity against SH reagents is also not seen. The optimum pH of the enzyme is 6.8.

The molecular weight of the carbamate hydrolase is in the range of 50–60, preferably 53–57 kd, both under denaturing/dissociating conditions (SDS gel electrophoresis) as well as under native conditions (gel filtration). From this it follows that the carbamate hydrolase is a monomeric protein. The isoelectric point of the carbamate hydrolase is at pI=6.2.

EXAMPLE 3

Process for detecting the carbamate hydrolase.

For a quick and sure determination of enzyme activity during the purification of the crude protein extracts, an in vitro enzyme test was developed. The test is based on the ability of the enzyme to change the highly water insoluble phenmedipham into a soluble hydrolysis product. For this, solid phenmedipham was suspended in water and micronized by ultrasound. This micro-suspension was then poured, with stirring at 50° C., into an agarose solution and this mixture put into a petri dish before it solidified, where it formed into a turbid gel matrix. The enzyme solution was then put into wells which had been punched in the solid matrix. After incubation of the test plates for 2–4 hours at 30° C., the enzyme activity ws demonstrated by observing clear zones in the matrix which had been made opaque by the phenmedipham.

EXAMPLE 4

Identification of the amino acid sequence of two BrCN cleaving peptides and synthesis of oligonucleotides for specific evidence of the carbamate hydrolase gene by hybridization.

Resulting from the purified carbamate hydrolase, two peptides were isolated after BrCN cleavage, whose partial sequence was established by Edman degradation.

BrCN Peptide I (Seq ID No. 1):
H$_2$N-Ser-Asp-Glu-Phe-Ala-Asn-Leu-Asp-Arg-Trp-Thr-Gly-Lys-Pro-Phe-Val-Asp (Val)-Gly (His)-Leu-Asp-Glu-Val-Ala-Val-COOH BrCN Peptide II (Seq ID No. 2):
N$_2$H-Glu-His-Thr-Lys-Phe(Val)-Asn(Gly)-Glu-Arg(Cys)-Pro-Leu-Ala-Phe-Tyr-Pro-Val-Phe-Asn-Glu-COOH According to the amino acid sequence information of these peptides, oligonucleotides were synthesized which could be used as hybridization probes for the detection of the carbamate hydrolase gene:

Oligonucleotide I (Seq ID No. 3) (17 mer "mixed probe") contains as the single strand DNA fragment, the sequence information of the BrCN peptide I amino acid position 10–15 (complementary strand).

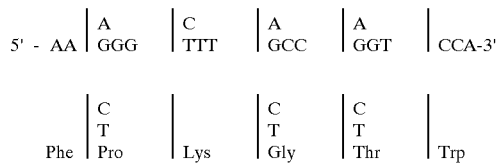

Oligonucleotide II (Seq ID No. 4) (42 mer) contains as a single strand DNA fragment, the sequence information of the BrCN peptide I amino acid position 8–21 (complementary strand). The codon selection was carried out under the assumption of a guanine(G) and cytosine(C) rich DNA sequence (this takes into consideration guanine (G) and cytosine(C) nucleotides before adenine(A) and thiamine(T) nucleotides on the third position of the triplets).

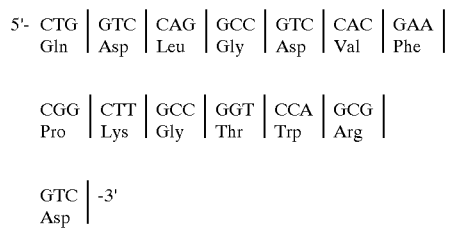

Oligonucleotide III (Seq ID No. 5) contains as the single strand DNA fragment sequence, information of the BrCN peptide II (complementary strand).

By using these oligonucleotides it was possible to localize the carbamate hydrolase gene within the plasmid pHP52 by hybridization. For this, the plasmid DNA was cleaved with restriction endonucleases and the resulting fragments were separated by agarose gel electrophoresis and then transferred according to the method of E. M. Southern (J. Mol. Biol. 98, 503–17 (1975)) in single strand form on membrane filters (Gene Screen Plus™ hybridizing membrane, Du Pont de Nemours/NEN Research Products).

The oligonucleotides were end marked by use of T4-polynucleotide kinase (Boehringer Mannheim) and [γ-$^{32}$P]-adenosine-5'-triphosphate (>5000 Ci/mmol, Du Pont de Nemours/NEN Research Products) using the method of R. B. Wallace and C. G. Miyada, Methods in Enzymology 152, 432–442 (1987) and treated without further purification for the hybridization.

The hybridization was carried out using standard processes (P. J. Mason & J. G. Williams in "Nucleic Acid Hybridization" p. 113–160 (1985) B. D. Hames & S. J. Higgins Hrsg. IRL Press Oxford, Washington, D.C.). Under the conditions 6×SSC, 10×Denhardt, 0.5% w/v SDS and 100 u/ml t RNA (Beckerhefe, Boehringer Mannheim), as well as 10 ng/ml marked oligonucleotides I/II/III at 41° C. (=6 hours), a specific hybridization can be achieved. The detection of the hybrids was carried out by autoradiography (T Maniatis, E F Fritsch & J Sambrook, "Molecular Cloning", Cold Spring Harbor Laboratory (1982)).

EXAMPLE 5

Isolation and characterization of the plasmid pHP52 from *Arthrobacter oxidans* P52.

For isolation of plasmid pH52 from Arthrobacter, the alkali extraction method of Birnboim and Doly (Birnboim H. C. & Doly J. (1979) Nucl. Acid Res., 7, 1513–1523) was used, with a modification by Brandsch and Decker (Brandsch, R. & Decker, K. (1984) Arch. Microbiol. 138, 15–17). For plasmid preparation, the bacteria were cultivated in 6 liters of LB-medium comprising:

| | |
|---|---|
| Bacto-trypton (Difco ®) | 10 g/l |
| Bacto-Yeast-Extract (Difco ®) | 5 g/l |
| NaCl | 10 g/l | to a cell density of OD$_{550}$=1.4 and harvested by centrifuging.

The cells were resuspended in a total of 210 ml solution I (50 mM glucose; 10 mM EDTA; 25 mM Tris/HCl, pH 8.0; 1 mg/ml lysozyme) and incubated for 1 hour at room temperature. Lysis was carried out by addition of 360 ml solution II (0.2M NaOH; 1% SDS). After gentle but thorough mixing and subsequent incubation for 5 minutes at room temperature, followed by cooling on ice for 5 minutes, the mixture was neutralized by the addition of 180 ml solution III (2M Tris/HCl, pH 7.0/0.5M KCl. After incubation for 1 hour on ice, the undissolved precipitate was separated by centrifugation. The plasmid DNA was precipitated from the clear supernatant by addition of 0.6 volumes isopropanol and, after an incubation of 15 minutes at room temperature, pelleted by centrifugation (15,000×g/30 minutes). The plasmid-containing precipitate was dried in vacuo and dissolved in 24 ml 10×TE buffer (100 mM Tris/HCl, pH 8.0; 10 mM EDTA). This plasmid containing solution was then purified by isopycnic cesium chloride density gradient, centrifuging in the presence of Ethidium bromide (Maniatis T., Fritsch E. F. & Sambrook J. in "Molecular Cloning" (1982), Cold Spring Harbor N.Y.).

Purified plasmid DNA was mapped by restriction analysis which cut the plasmid once or gave several fragments. These fragments were resolved by agarose gel electrophoresis (0.8% w/v). Molecular weight standards used in mapping plasmid DNA were Hind III or Hind III and EcoRI digested bacteriophage DNA.

The restriction analysis data were consistent with a circular map of pHP52 (FIG. 4). The size of the plasmid is the sum of individual restriction fragments.

All the processes were carried out in this Example according to standard methods (cf. Maniatis T., Fritsch E. F. & Sambrook J. in "Molecular Cloning" Cold Spring Harbor, N.Y. (1982)).

EXAMPLE 6

Identification of the coding region of the carbamate hydrolase gene by oligonucleotide hybridization.

By hybridization of the restriction fragments of the plasmid pHP52 separated by gel electrophoresis and transferred on membrane filters with the $^{32}P$ marked oligonucleotide described in Example 4, the position of the coding region of the carbamate hydrolase gene can be definitely correlated on the restriction map of the plasmid pHP52. In FIG. 5, the hybridizing area is enlarged. All three oligonucleotides hybridize with the central part of a PstI restriction fragment of size 3.3 kb. In FIG. 6, a detailed restriction map of the fragment is shown from which the exact positions of the hybridizing areas can be seen.

EXAMPLE 7

Cloning of the carbamate hydrolase gene in *E. coli* and demonstration of the genes' expression under Lac promoter control.

For cloning the carbamate hydrolase gene in *E. coli* the vector pUC19 (Yannish-Perron, C., Vieira, J., & Messing, J. (1985) Gene 33, 103ff) was used. The pUC19 DNA was linearized by cleavage with restriction nuclease PstI and treated with alkaline phosphatase. The DNA of the 3.3 kb long PstI restriction fragment of the plasmid pHP52 was isolated (after digesting the wild-type plasmid DNA with PstI) by preparative agarose gel electrophoresis. The linearized and dephosphorylated vector DNA and the 3.3 kb long PstI fragment was then ligated with T4 DNA ligase. *E. coli* DH5α was transformed with the ligation mixture.

Two types of clones were obtained which contained the fragment in different orientations to the transcription direction of the lac Z' gene of the vector pUC 19. These are the clones pp52 Pst and pp52 Pst inv. The restriction map of both clones is shown in FIG. 5. The clones of type *E. coli* pp52 Pst express carbamate hydrolase, after addition of the inductor isopropyl-β-D-thiogalactopyranosid to the culture medium. Without inducer addition (repressed state of the Lac promoter) to logarithmic cultures of the clone pp52 Pst as well as by repressed and induced logarithmic cultures of the clone pp52 Pst inv in enzyme extracts, no enzyme activity was seen using the assays described in Example 3.

This means that the carbamate hydrolase gene in clones of type pp52 Pst lies in the same transcription direction (5'-3' orientation) as the lac Z' gene of the vector. The Arthrobacter promoter is not or only slightly expressed in *E. coli*.

EXAMPLE 8

Nucleotide sequence of the carbamate hydrolase gene from the *Arthrobacter oxidans* (species P52) and the deduced protein sequence.

The nucleotide sequence of the carbamate hydrolase gene was established by the method of Sanger (Sanger F., Nicklen S. & Coulson A. (1977) Proc. Natl. Acad. Sci. USA, 74, 5463–5468).

For this, 15 sub-clones in the single stranded DNA bacteriophage M13 mp18 and M13 mp19 from the pp52 PST DNA were constructed (Messing, J. (1983) Methods in Enzymol, 101, 20–78). After transfection of *E. coli* DH5αF', the sequence of the single stranded recombinant DNA was established.

In FIG. 6, the sequencing strategy of the carbamate hydrolase gene is shown. Altogether the sequence of 1864 base pairs was established.

In FIGS. 7A to 7D (Seq ID No. 6), the established nucleotide sequence is shown with the deduced amino acid sequence of the carbamate hydrolase. The reading frame is clearly defined as described by the amino acid sequences of two BrCN cleavage peptides as described in Example 4. The reading frame finishes with a TGA stop codon (nucleotide position 1789–1791 in FIGS. 7A to 7D (Seq ID No. 6)). As a translation start codon, a GTG (nucleotide position 310–312) is suitable. This gives the longest open reading frame of 1479 bp (=493 amino acids). All open reading frames which begin with the usual ATG start codons give no protein of suitable size (compared to the molecular weight determination of the protein).

The hypothesis that translation starts from GTG (position 310–312) is further supported by the existence of a definite homologous region to the consensus sequence for ribosomal *E. coli* binding sites 7 bp upstream of the putative GTG start codon.

All cloning steps were carried out by standard processes (cf Maniatis, T., Fritsch, E. F. & Sambrook, J. (1982) in "Molecular Cloning", Cold Spring Harbor, N.Y.). The sequencing reactions were carried out using Sequenase® DNA Sequencing Kits (United States Biochemical Corporation) according to information by the producer. The separation of the marked reaction products was carried in 6% w/v polyacrylamide/urea gel (Maxam, A. M. & Gilbert, W. (1980) Methods Enzymol. 65, 497–559).

EXAMPLE 9

Construction of plasmids for the expression of carbamate hydrolase in plants.

a) Construction of intermediate vectors

Plasmid DNA from pp52Pst (FIG. 8) is methylated using TaqI Methylase (M. TaqI) to make the single SalI restriction site inaccessible to HindII. Then the methylated plasmid is cut with both restriction enzymes XbaI and HindII to release a 2.2 kb DNA fragment containing the open reading frame for carbamate hydrolase. This fragment is purified by preparative agarose gel electrophoresis. The vector plasmid pA5 (FIG. 8) is cut with XbaI and HindII and then ligated with the purified 2.2 kb DNA fragment, thus linking the 3'-end of the carbamate hydrolase coding region to the polyadenylation signal of the octopine synthetase (OCS) gene (Dhaese et al., EMBO J. 2:419, 1983). Competent cells of *E. coli* DH5alpha are transformed with the recombined DNA and clones are selected on LB-agar containing 100 µg/ml carbenicillin. Clones containing the recombined plasmid pUPA1014 (FIG. 8) are identified by restriction analysis of isolated plasmid DNA.

Two oligonucleotides of the following sequence are synthesized by an automatic synthesizer:
1) 5'-CTAGAGATCT CAACAATGGT TACCAGACCG ATCGCCCACA CCACCGCTGG G-3' (Seq ID No. 8)
2) 5'-GTCCCCAGCG GTGGTGTGGG CGATCGGTCT GGTAACCATT GTTGAGATC-3' (Seq ID No. 9)

They represent complementary DNA strands which are able to reconstitute the N-terminal portion of the open reading frame of the carbamate hydrolase gene upstream (5') of the PpuMI restriction site.

Both complementary oligonucleotides are mixed, phosphorylated by polynucleotide kinase and then annealed by shifting temperature from 70° C. to room temperature overnight. Plasmid DNA of pUPA1014 is digested with XbaI and then ligated with the annealed oligonucleotide. This covalently links two oligonucleotides at their XbaI-compatible ends to both ends of the linearized plasmid. The linear ligation product is purified by preparative agarose gel electrophoresis and digested with PpuMI to remove the N-terminal part of the coding region. The linear DNA is then recircularized by ligase treatment. Competent cells of *E. coli* DH5alpha are transformed with the recombined DNA and clones are selected on LB-agar containing 50 µg/ml carbenicillin. Clones containing the recombined plasmid pUP01015 (FIG. 9) are identified by restriction analysis of isolated plasmid DNA. The correct ligation of the oligonucleotide is verified by sequence analysis of purified pUP01015 DNA using the dideoxy method (Sanger et al., Proc. Natl. Acad. Sci. USA 74:5463, 1977) modified for plasmid DNA as template (Chen and Seeburg, DNA 4:165, 1985).

b) Construction of plasmids for the cytoplasmatic expression of carbamate hydrolase.

Plasmid DNA of pUP01015 is digested with both restriction enzymes XbaI and HindIII to create a DNA fragment that contains the whole recombinant coding region of the carbamate hydrolase together with the polyadenylation signal described above. The fragment is then ligated with the plant expression vector plasmid pA8 (A. v. Schaewen, Dissertation, FU Berlin, 1989; FIG. 10) which was similarly treated with XbaI and HindIII. The ligation links the gene in correct orientation to the cauliflower mosaic virus (CaMV) 35S promoter (Paszkowski et al., EMBO J. 3:2717, 1984) contained in pA8. Competent cells of *E. coli* DH5alpha are transformed with the recombined DNA and clones are selected on LB-agar containing 25 µg/ml streptomycin. Clones containing the recombined plasmid pMCP01021 (FIG. 10) are identified by restriction analysis of isolated plasmid DNA.

Plasmid DNA of pMCPO1021 is digested with both restriction enzymes EcoRI and HindIII to create a DNA fragment that contains the CaMV 35S promoter, the carbamate hydrolase coding region and the OCS polyadenylation signal. The fragment is then ligated with a EcoRI and HindIII cleaved vector plasmid pBIN19 that is part of the binary transformation system described by Bevan, Nucl. Acids Res. 12:8711, 1984. Competent cells of *E. coli* S17-1 (Simon et al. Bio/Technology 1:784–791, 1983) are transformed with the recombined DNA and clones are selected on LB-agar containing 50 µg/ml kanamycin. Clones containing the recombined plasmid pBCPO1027 are identified by restriction analysis of isolated plasmid DNA.

c) Construction of plasmids for the extracellular expression of carbamate hydrolase.

Plasmid pA22 (FIG. 11) contains a synthetic intronless sequence that codes for the signal peptide of the proteinase inhibitor II(PI) from potato and can be attached to the N-terminus of other genes to direct the gene product into the endoplasmic reticulum of the plant cell. To create an intermediate vector for targeting of carbamate hydrolase, the DNA fragment encoding the signal peptide is excised from plasmid pA22 by cleavage with restriction enzymes KpnI and XbaI and then ligated with a KpnI and XbaI cleaved plasmid pA8. Competent cells of *E. coli* DH5alpha are transformed with the recombined DNA and clones are selected on LB-agar containing 25 µg/ml streptomycin. Streptomycin resistant clones are then screened for the loss of plasmid pA22 on LB-agar containing 50 µg/ml carbenicillin. Carbenicillin sensitive clones are analyzed by restriction analysis of isolated plasmid DNA and recombined plasmids containing the signal peptide encoding sequence are designated pmA 1017 (FIG. 11).

Plasmid DNA of pUP01015 is digested with both restriction enzymes HindIII and BglII to create a DNA fragment that contains the whole recombinant coding region of the carbamate hydrolase together with the polyadenylation signal described above. The fragment is then ligated with the plant expression vector plasmid pMA1017 which has been digested with BamHI and HindIII. The ligation links the gene in correct orientation to the cauliflower mosaic virus (CaMV) 35S promotor (Paszkowski et al., EMBO J. 3:2717, 1984) and the proteinase inhibitor signal sequence described above. Competent cells of *E. coli* DH5alpha are transformed with the recombined DNA and clones are selected on LB-agar containing 25 µg/ml streptomycin. Clones containing the recombined plasmid pMAP01022 (FIG. 12) are identified by restriction analysis of isolated plasmid DNA.

Plasmid DNA of pMAP01022 is digested with both restriction enzymes EcoRI and HindIII to create a DNA fragment that contains the CaMV 35S promoter, the PI signal sequence linked in frame to the carbamate hydrolase coding region and the OCS polyadenylation signal. The fragment is then ligated with a EcoRI and HindIII cleaved vector plasmid pBIN19 (Bevan, Nucl. Acids Res. 12:8711, 1984). Competent cells of *E. coli* S17-1 (Simon et al. Bio/Technology 1:784–791, 1983) are transformed with the recombined DNA and clones are selected on LB-agar containing 50 µg/ml kanamycin. Clones containing the recombined plasmid pBAP01027 are identified by restriction analysis of isolated plasmid DNA.

EXAMPLE 10

Transformation of tobacco with chimeric carbamate hydrolase genes.

a) Transfer of recombinant carbamate hydrolase from *E. coli* to *A. tumefaciens*

Strains of *E. coli* S17-1 containing chimeric carbamate hydrolase genes on plasmids pBCP01027 or pBAP01028 are grown at 37° C. in liquid LB medium containing 50 µg/ml kanamycin. *Agrobacteria tumefaciens* LBA4404 (Bevan, Nucl. Acids Res. 12:8711, 1984) is grown at 28° C. in liquid YEB medium (Yeast extract 1 g/l, beef extract 5 g/l, peptone 5 g/l, sucrose 5 g/l, sucrose 5 g/l, $MgSO_4$ 0.5g/l). 0.4 ml samples of *E. coli* culture are centrifuged and the bacterial pellets are resuspended in 0.4 ml YEB. Bacterial suspensions of *E. coli* in YEB and samples of *Agrobacterium tumafaciens* culture in YEB are then mixed in a 1:1 ratio in relation to cell density. Samples of 50–100 µl from the mixtures are spotted onto LB-agar and incubated at 28° C. for 6–16 hours. Bacterial mating mixtures that have grown on the agar are suspended in liquid M9-salts (6 g/l $Na_2HPO_4$, 3 g/l $KH_2PO_4$, 0.5 g/l NaCl, 1 g/l $NH_4Cl$, 2 MM $MgSO_4$, 0.1 mM $CaCl_2$, 1 mM thiamine, HCl) and then plated in several dilutions onto M9-agar containing 2 g/l sucrose and 50 µg/ml kanamycin. Plates are incubated at 28° C. for several days until bacterial colonies have grown. These colonies are further purified by subsequent cultivation on the same medium. That these clones of *A. tumefaciens* LBA4404 contain recombinant plasmids pBCP01027 and pBAP01028 respectively is verified by restriction analysis of isolated plasmid DNA.

b) Transfer of recombinant carbamate hydrolase from *A. tumefaciens* to tobacco.

For transformation of tobacco, *A. tumefaciens* strains harboring carbamate hydrolase plasmids are grown overnight at 28° C. in liquid YEB medium containing 50 µg/ml kanamycin. Cells are centrifuged at 5000 g for 15 minutes and resuspended in the same volume of YEB without antibiotic. *Nicotiana tabacum* Wisconsin W38 plantlets are grown under sterile conditions on solid MS medium containing 20 g/l sucrose. Leaves are cut from those plants, dissected into pieces of around 1 $cm^2$ and rinsed with the bacterial suspension. Leaf disks are then placed onto solid MS medium containing 20 g/l sucrose. After 2 days of incubation at room temperature in the dark, leaf disks are transferred to solid MS medium containing 16 g/l glucose, 1 mg/l benzylaminopurine, 0.2 mg/l naphthylacetic acid, 500 mg/l claforan and 50 mg/l kanamycin. Incubation is continued at 25° C under a daily regime of 16 hours light (photosynthetically active radiation=67 $\mu EM^{-2}s^{-1}$) and 8 hours dark. The medium is changed every week until shoots appear. These are cut from the callus and transferred to MS medium containing 20 g/l sucrose and 250 mg/l claforan. Incubation is continued under the same conditions until roots of 1–2 cm in length have formed and plants are transferred to soil. Total RNA isolated from leaves is analyzed by northern blot hybridization using the 1.8 kb EcoRI-HindIII fragment of pUP01015 as a labeled probe. Transformed plants synthesize a transcript of around 1.8 kb in size that specifically hybridizes with the carbamate hydrolase coding sequence.

EXAMPLE 11

Detection of transformed plants which are resistant to the herbicidal activity of phenmedipham.

Transgenic plants are transferred to soil and grown in a growth chamber at 25° C. with a day/night rhythm of 16 hours light and 8 hours dark. No difference in growth can be seen between transformed and untransformed tobacco. Plants that have a leaf length of around 10 cm are sprayed with the herbicide Betanal® (active ingredient: 157 g/l phenmedipham).

Doses corresponding to field application rates of 1 kg/ha, 3 kg/ha and 10 kg/ha are used to distinguish between resistant plants and untransformed wildtype plants: Whereas 1 kg/ha is completely lethal for wildtype plants, transgenic plants which express the carbamate hydrolase gene show resistance levels between 1 kg/ha and 10 kg/ha (FIGS. 13A to 13C).

The same spraying experiment is done by using Betanal® AM (active ingredient: 157 g/l desmedipham) as 2.0 the herbicidal agent.

EXAMPLE 12

Analysis of herbicide detoxification in plants sprayed with phenmedipham.

Transgenic tobacco plants expressing carbamate hydrolase and untransformed control plants are grown as described in Example 11 and sprayed with the herbicide Betanal® corresponding to 1 kg/ha phenmedipham. Normalized variable fluorescence is measured on intact leaves of sprayed plants as is described by Voss, Weed Science 32:675–680 (1984). The equipment used is a Kompakt Fluorometer RKF 1000 (Ingenieurburo F.U.R. Dr. M. Voss, Berlin). Measurement values before spraying are taken as 100% relative variable fluorescence. Subsequent measurements are performed in a time course of 2, 4, 8, 24 hours and then every day up to 4 days. Relative variable fluorescence values of transgenic tobacco plants expressing carbamate hydrolase stay constantly higher than 90%; in contrast values from untransformed tobacco fall below 10% within the first 8 hours after spraying (FIG. 15).

The same spraying experiment is done by using Betanal® AM (active ingredient: 157 g/l desmedipham) as the herbicidal agent.

Although the present invention has been described in relation to particular embodiments thereof, many other variations and modifications and other uses will become apparent to those skilled in the art. Therefore, the present invention is to be limited not by the specific disclosure herein, but only by the appended claims.

What is claimed is:

1. A purified *Arthrobacter oxidans* carbamate hydrolase peptide, comprising at least one amino acid sequence selected from the group consisting of:

Peptide I (SEQ ID NO:1):
H$_2$N-Ser-Asp-Glu-Phe-Ala-Asn-Leu-Asp-Arg-Trp-Thr-Gly-Lys-Pro-Phe-Val-Asp (Val)-Gly (His)-Leu-Asp-Glu-Val-Ala-Val-COOH and Peptide II (SEQ ID NO:2):
N$_2$H-Glu-His-Thr-Lys-Phe(Val)-Asn(Gly)-Glu-Arg(Cys)-Pro-Leu-Ala-Phe-Tyr-Pro-Val-Phe-Asn-Glu-COOH.

2. A purified carbamate hydrolase isolatable from *Arthrobacter oxidans* having a molecular weight in the range of approximately 50–60 kd, an isoelectric point of approximately pI=6.2, and a pH optimum of approximately 6.8.

3. A DNA fragment encoding an amino acid sequence selected from the group consisting of SEQ ID NO:1 and SEQ ID NO:2.

4. An oligonucleotide consisting essentially of a sequence selected from the group consisting of:

Oligonucleotide I (SEQ ID NO:3):

```
         A    C   A   A
5'-AA   GGG  TTT GCC GGT  CCA-3'
         C        C   C
         T        T   T
     Phe Pro  Lys Gly Thr Trp ,
```

Oligoucleotide II (SEQ ID NO:4):

```
5'-CTG  GTC  CAG GCC GTC CAC GAA
    Gln Asp  Leu Gly Asp Val Phe
    CGG CTT  GGC GGT CCA GCG
    Pro Lys  Gly Thr Trp Arg
    GTC -3'
    Asp , and
```

Oligonucleotide III (SEQ ID NO:5):

```
5'-TTC  GTT  GAA GAC CGG GTA GAA CGC
    Gln Asn  Phe Val Pro Tyr Phe Ala .
```

5. A method for the isolation of carbamate hydrolase from *Arthrobacter oxidans,* comprising the steps of:

a) running a supernatant of a centrifuged homogenate of disrupted cells of *Arthrobacter oxidans* on an anion exchange column;

b) precipitating enzymatically active fractions of the eluate of step a) by ammonium sulphate; and c) putting the dissolved, enzymatically active precipitate of step b) through gel filtration to isolate a carbamate hydrolase.

6. A process for the isolation and subsequent purification of carbamate hydrolase from *Arthrobacter oxidans* comprising:

a) running a supernatant of a centrifuged homogenate of disrupted cells of *Arthrobacter oxidans* on an anion exchange column;

b) precipitating enzymatically active fractions of the eluate of step a) by ammonium sulphate;

c) putting the dissolved, enzymatically active precipitate of step b) through gel filtration; and d) further purifying the enzymatically active fractions resulting from step c) by FPLC separation to obtain an electrophoretically homogeneous carbamate hydrolase.

7. A method of isolating a carbamate hydrolase gene from *Arthrobacter oxidans* comprising the steps of:

probing a gene library with a nucleotide fragment selected from the group consisting of SEQ ID NO:3, SEQ ID NO:4 and SEQ ID NO:5, and fragments thereof, under conditions that allow specific hybridization to a carbamate hydrolase gene:

and isolating a hybridizing carbamate hydrolase gene.

8. A method of isolating a carbamate hydrolase gene from *Arthrobacter oxidans* comprising the steps of:

probing a gene library with a nucleotide fragment encoding an amino acid sequence selected from the group consisting of SEQ ID NO: 1,SEQ ID NO:2, and fragments thereof, under conditions that allow specific hybridization to a carbamate hydrolase gene;

and isolating a hybridizing carbamate hydrolase gene.

* * * * *

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
        ( A ) LENGTH: 24 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: internal ( v i ) ORIGINAL SOURCE:
        ( A ) ORGANISM: Arthrobacter oxidans
        ( B ) STRAIN: P52

( x i ) SEQUENCE DESCRIPTION: SEQ ID NO:1:

```
Ser  Asp  Glu  Phe  Ala  Asn  Leu  Asp  Arg  Trp  Thr  Gly  Lys  Pro  Phe  Val
1                  5                            10                           15

Xaa  Xaa  Leu  Asp  Glu  Val  Ala  Val
                20
```

( 2 ) INFORMATION FOR SEQ ID NO:2:

( i ) SEQUENCE CHARACTERISTICS:
        ( A ) LENGTH: 18 amino acids
        ( B ) TYPE: amino acid ( C ) STRANDEDNESS: single
( D ) TOPOLOGY: linear ( i i ) MOLECULE TYPE: protein ( i i i ) HYPOTHETICAL: NO ( i v ) ANTI-SENSE: NO ( v ) FRAGMENT TYPE: internal ( v i ) ORIGINAL SOURCE:
( A ) ORGANISM: Arthrobacter oxidans
( B ) STRAIN: P52

( x i ) SEQUENCE DESCRIPTION: SEQ ID NO:2:

```
Glu  His  Thr  Lys  Xaa  Xaa  Glu  Xaa  Pro  Leu  Ala  Phe  Tyr  Pro  Val  Phe
1                  5                        10                       15

Asn  Glu
```

( 2 ) INFORMATION FOR SEQ ID NO:3:

( i ) SEQUENCE CHARACTERISTICS:
( A ) LENGTH: 17 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: YES ( i v ) ANTI-SENSE: NO ( v i ) ORIGINAL SOURCE:
( A ) ORGANISM: Arthrobacter oxidans
( B ) STRAIN: P52

( x i ) SEQUENCE DESCRIPTION: SEQ ID NO:3:

AANGGYTTNC CNGTCCA                                                                              17

( 2 ) INFORMATION FOR SEQ ID NO:4:

( i ) SEQUENCE CHARACTERISTICS:
( A ) LENGTH: 42 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: YES ( i v ) ANTI-SENSE: NO ( v i ) ORIGINAL SOURCE:
( A ) ORGANISM: Arthrobacter oxidans
( B ) STRAIN: P52

( x i ) SEQUENCE DESCRIPTION: SEQ ID NO:4:

CTGGTCCAGG CCGTCCACGA ACGGCTTGCC GGTCCAGCGG TC                                                   42

( 2 ) INFORMATION FOR SEQ ID NO:5:

( i ) SEQUENCE CHARACTERISTICS:
( A ) LENGTH: 24 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: YES (i v) ANTI-SENSE: NO (v i) ORIGINAL SOURCE:
    (A) ORGANISM: Arthrobacter oxidans
    (B) STRAIN: P52

(x i) SEQUENCE DESCRIPTION: SEQ ID NO:5:

```
TTCGTTGAAG  ACCGGGTAGA  ACGC                                                24
```

(2) INFORMATION FOR SEQ ID NO:6:

(i) SEQUENCE CHARACTERISTICS:
        (A) LENGTH: 1864 base pairs
        (B) TYPE: nucleic acid
        (C) STRANDEDNESS: double
        (D) TOPOLOGY: linear (i i) MOLECULE TYPE: DNA (genomic)

(i i i) HYPOTHETICAL: NO (i v) ANTI-SENSE: NO (i x) FEATURE:
        (A) NAME/KEY: RBS
        (B) LOCATION: 298..302

(i x) FEATURE:
        (A) NAME/KEY: CDS
        (B) LOCATION: 310..1791
        (D) OTHER INFORMATION: /codon=(seq: "gta", aa: Val)
            / product= "carbamate hydrolase"
            / transl_except=(pos: 310 .. 312, aa: Met)
            / note= "terminator (1789-1791)"

(i x) FEATURE:
        (A) NAME/KEY: mat_peptide
        (B) LOCATION: 310..1788

(x i) SEQUENCE DESCRIPTION: SEQ ID NO:6:

```
TCCTTGCCAG  TCACGGCACC  CCAGCCAACC  CGGAAGTGGC  ACCTGCTCGG  GCACATCGGT        60

GCGAACGCTT  CGTCCTGATT  CCGATGCCAA  CTGCTTGACG  GCCGTGACAC  ATATGTAGCA       120

TAGTCGCCTA  GCATGGACCC  GCAGCACACC  TGCTGTCGGC  TCCCGCGCTA  TCCCCGACCA       180

GCGCCGGTCA  CGGGTAGTCC  TCGTGAGAGG  CACCAGAACG  ACAACGGCGC  ACTGTCCCGC       240

AACACGGCCG  TATAACCCCA  CCGGGGTCCG  CGCCCGAGCT  AGTTCTGGCT  CAACCATAAG       300

GAGAACCTC  GTG  ATT  ACC  AGA  CCG  ATC  GCC  CAC  ACC  ACC  GCT  GGG  GAC       348
           Met  Ile  Thr  Arg  Pro  Ile  Ala  His  Thr  Thr  Ala  Gly  Asp
            1             5                            10

CTC  GGC  GGT  TGC  CTT  GAA  GAC  GGC  CTG  TAC  GTG  TTC  CGA  GGA  GTG  CCG   396
Leu  Gly  Gly  Cys  Leu  Glu  Asp  Gly  Leu  Tyr  Val  Phe  Arg  Gly  Val  Pro
 15                  20                           25

TAC  GCC  GAG  CCG  CCG  GTC  GGC  GAC  CTG  CGG  TGG  CGG  GCG  GCG  CGC  CCG   444
Tyr  Ala  Glu  Pro  Pro  Val  Gly  Asp  Leu  Arg  Trp  Arg  Ala  Ala  Arg  Pro
 30                       35                           40                  45

CAC  GCC  GGC  TGG  ACC  GGC  GTC  CGC  GAC  GCC  TCC  GCG  TAT  GGT  CCC  TCG   492
His  Ala  Gly  Trp  Thr  Gly  Val  Arg  Asp  Ala  Ser  Ala  Tyr  Gly  Pro  Ser
                       50                       55                       60

GCG  CCG  CAA  CCC  GTG  GAG  CCT  GGC  GGC  TCG  CCG  ATC  CTT  GGG  ACA  CAC   540
Ala  Pro  Gln  Pro  Val  Glu  Pro  Gly  Gly  Ser  Pro  Ile  Leu  Gly  Thr  His
                  65                       70                       75

GGC  GAC  CCT  CCG  TTT  GAC  GAG  GAC  TGC  CTG  ACT  CTC  AAT  CTT  TGG  ACC   588
Gly  Asp  Pro  Pro  Phe  Asp  Glu  Asp  Cys  Leu  Thr  Leu  Asn  Leu  Trp  Thr
             80                       85                       90
```

| | | | | | | | | | | | | | | | | |
|---|---|---|---|---|---|---|---|---|---|---|---|---|---|---|---|---|
| CCG | AAC | CTC | GAC | GGC | GGT | AGC | CGG | CCG | GTC | CTC | GTC | TGG | ATC | CAT | GGT | 636 |
| Pro | Asn | Leu | Asp | Gly | Gly | Ser | Arg | Pro | Val | Leu | Val | Trp | Ile | His | Gly | |
| | 95 | | | | 100 | | | | | 105 | | | | | | |
| GGG | GGC | CTA | CTA | ACC | GGC | TCG | GGA | AAT | CTA | CCT | AAC | TAC | GCG | ACC | GAT | 684 |
| Gly | Gly | Leu | Leu | Thr | Gly | Ser | Gly | Asn | Leu | Pro | Asn | Tyr | Ala | Thr | Asp | |
| 110 | | | | | 115 | | | | | 120 | | | | | 125 | |
| ACC | TTC | GCC | CGC | GAC | GGC | GAC | TTG | GTA | GGT | ATC | TCA | ATC | AAT | TAC | CGG | 732 |
| Thr | Phe | Ala | Arg | Asp | Gly | Asp | Leu | Val | Gly | Ile | Ser | Ile | Asn | Tyr | Arg | |
| | | | | 130 | | | | | 135 | | | | | 140 | | |
| CTC | GGG | CCT | CTT | GGA | TTC | CTC | GCA | GGA | ATG | GGC | GAC | GAG | AAT | GTC | TGG | 780 |
| Leu | Gly | Pro | Leu | Gly | Phe | Leu | Ala | Gly | Met | Gly | Asp | Glu | Asn | Val | Trp | |
| | | | 145 | | | | | 150 | | | | | 155 | | | |
| CTC | ACC | GAT | CAG | GTA | GAG | GCA | CTG | CGC | TGG | ATT | GCA | GAT | AAC | GTT | GCT | 828 |
| Leu | Thr | Asp | Gln | Val | Glu | Ala | Leu | Arg | Trp | Ile | Ala | Asp | Asn | Val | Ala | |
| | | 160 | | | | | 165 | | | | | 170 | | | | |
| GCC | TTC | GGT | GGA | GAC | CCG | AAC | CGG | ATC | ACT | CTC | GTC | GGT | CAA | TCA | GGC | 876 |
| Ala | Phe | Gly | Gly | Asp | Pro | Asn | Arg | Ile | Thr | Leu | Val | Gly | Gln | Ser | Gly | |
| | 175 | | | | | 180 | | | | | 185 | | | | | |
| GGG | GCA | TAC | TCG | ATC | GCA | GCG | CTC | GCC | CAA | CAC | CCG | GTC | GCC | CGT | CAG | 924 |
| Gly | Ala | Tyr | Ser | Ile | Ala | Ala | Leu | Ala | Gln | His | Pro | Val | Ala | Arg | Gln | |
| 190 | | | | | 195 | | | | | 200 | | | | | 205 | |
| CTG | TTC | CAC | CGC | GCG | ATC | CTA | CAA | AGC | CCA | CCA | TTC | GGG | ATG | CAA | CCC | 972 |
| Leu | Phe | His | Arg | Ala | Ile | Leu | Gln | Ser | Pro | Pro | Phe | Gly | Met | Gln | Pro | |
| | | | | 210 | | | | | 215 | | | | | 220 | | |
| CAT | ACA | GTT | GAA | GAA | TCG | ACG | GCA | AGG | ACG | AAG | GCC | CTG | GCC | CGG | CAT | 1020 |
| His | Thr | Val | Glu | Glu | Ser | Thr | Ala | Arg | Thr | Lys | Ala | Leu | Ala | Arg | His | |
| | | | 225 | | | | | 230 | | | | | 235 | | | |
| CTC | GGG | CAC | GAT | GAC | ATC | GAG | GCC | CTG | CGC | CAT | GAG | CCG | TGG | GAG | AGG | 1068 |
| Leu | Gly | His | Asp | Asp | Ile | Glu | Ala | Leu | Arg | His | Glu | Pro | Trp | Glu | Arg | |
| | | 240 | | | | | 245 | | | | | 250 | | | | |
| CTG | ATT | CAA | GGC | ACG | ATA | GGC | GTC | CTG | ATG | GAA | CAC | ACC | AAA | TTT | GGC | 1116 |
| Leu | Ile | Gln | Gly | Thr | Ile | Gly | Val | Leu | Met | Glu | His | Thr | Lys | Phe | Gly | |
| | 255 | | | | | 260 | | | | | 265 | | | | | |
| GAA | TGG | CCC | CTG | GCA | TTC | TAT | CCG | GTG | TTC | GAT | GAG | GCA | ACG | ATA | CCT | 1164 |
| Glu | Trp | Pro | Leu | Ala | Phe | Tyr | Pro | Val | Phe | Asp | Glu | Ala | Thr | Ile | Pro | |
| 270 | | | | | 275 | | | | | 280 | | | | | 285 | |
| CGC | CAT | CCG | ATT | GAG | TCC | ATT | ATC | GAT | TCC | GAC | ATC | GAA | ATC | ATC | ATC | 1212 |
| Arg | His | Pro | Ile | Glu | Ser | Ile | Ile | Asp | Ser | Asp | Ile | Glu | Ile | Ile | Ile | |
| | | | | 290 | | | | | 295 | | | | | 300 | | |
| GGC | TGG | ACA | CGC | GAC | GAG | GGC | ACT | TTT | CCG | TTT | GCC | TTC | GAC | CCT | CAG | 1260 |
| Gly | Trp | Thr | Arg | Asp | Glu | Gly | Thr | Phe | Pro | Phe | Ala | Phe | Asp | Pro | Gln | |
| | | | 305 | | | | | 310 | | | | | 315 | | | |
| GTT | TCA | CAG | GCG | GAT | CGC | GAT | CAG | GTC | GAG | TCA | TGG | TTG | CAG | AAG | CGT | 1308 |
| Val | Ser | Gln | Ala | Asp | Arg | Asp | Gln | Val | Glu | Ser | Trp | Leu | Gln | Lys | Arg | |
| | | 320 | | | | | 325 | | | | | 330 | | | | |
| TTC | GGA | GAC | CAC | GCC | GCC | TCG | TAC | GCC | TAC | GAG | GCT | CAC | GCC | GGC | GGA | 1356 |
| Phe | Gly | Asp | His | Ala | Ala | Ser | Ala | Tyr | Glu | Ala | His | Ala | Gly | Asp | Gly | |
| | 335 | | | | | 340 | | | | | 345 | | | | | |
| ACC | AGT | CCT | TGG | ACC | GTT | ATC | GCC | AAC | GTT | GTG | GGC | GAC | GAG | CTC | TTT | 1404 |
| Thr | Ser | Pro | Trp | Thr | Val | Ile | Ala | Asn | Val | Val | Gly | Asp | Glu | Leu | Phe | |
| 350 | | | | | 355 | | | | | 360 | | | | | 365 | |
| CAC | AGC | GCT | GGG | TAC | CGG | GTC | GCG | GAC | GAA | CGG | GCA | ACG | CGC | AGA | CCG | 1452 |
| His | Ser | Ala | Gly | Tyr | Arg | Val | Ala | Asp | Glu | Arg | Ala | Thr | Arg | Arg | Pro | |
| | | | | 370 | | | | | 375 | | | | | 380 | | |
| GTA | CGG | GCC | TAT | CAG | TTC | GAC | GTA | GTC | TCG | CCC | TTG | TCG | GAC | GGA | GCC | 1500 |
| Val | Arg | Ala | Tyr | Gln | Phe | Asp | Val | Val | Ser | Pro | Leu | Ser | Asp | Gly | Ala | |
| | | | 385 | | | | | 390 | | | | | 395 | | | |
| CTC | GGC | GCG | GTC | CAC | TGC | ATC | GAA | ATG | CCG | TTC | ACA | TTT | GCC | AAT | CTC | 1548 |
| Leu | Gly | Ala | Val | His | Cys | Ile | Glu | Met | Pro | Phe | Thr | Phe | Ala | Asn | Leu | |
| | | 400 | | | | | 405 | | | | | 410 | | | | |

| | | | | | | | | | | | | | | | | |
|---|---|---|---|---|---|---|---|---|---|---|---|---|---|---|---|---|
| GAC | CGT | TGG | ACG | GGG | AAG | CCG | TTC | GTG | GAC | GGC | CTG | GAT | CCA | GAC | GTG | 1596 |
| Asp | Arg | Trp | Thr | Gly | Lys | Pro | Phe | Val | Asp | Gly | Leu | Asp | Pro | Asp | Val | |
| 415 | | | | 420 | | | | | | 425 | | | | | | |
| GTG | GCT | CGG | GTG | ACC | AAC | GTG | TTG | CAT | CAG | GCC | TGG | ATC | GCA | TTC | GTC | 1644 |
| Val | Ala | Arg | Val | Thr | Asn | Val | Leu | His | Gln | Ala | Trp | Ile | Ala | Phe | Val | |
| 430 | | | | 435 | | | | | 440 | | | | | | 445 | |
| CGA | ACG | GGA | GAC | CCC | ACG | CAC | GAC | CAG | TTG | CCG | GTG | TGG | CCA | ACG | TTC | 1692 |
| Arg | Thr | Gly | Asp | Pro | Thr | His | Asp | Gln | Leu | Pro | Val | Trp | Pro | Thr | Phe | |
| | | | | 450 | | | | 455 | | | | | 460 | | | |
| CGA | GCG | GAC | GAC | CCA | GCG | GTG | TTG | GTC | GTC | GGC | GAC | GAG | GGA | GCA | GAG | 1740 |
| Arg | Ala | Asp | Asp | Pro | Ala | Val | Leu | Val | Val | Gly | Asp | Glu | Gly | Ala | Glu | |
| | | | 465 | | | | 470 | | | | | 475 | | | | |
| GTG | GCG | CGG | GAT | CTA | GCG | CGC | CCG | GAC | CAC | GTC | AGC | GTT | CGG | ACC | CTA | 1788 |
| Val | Ala | Arg | Asp | Leu | Ala | Arg | Pro | Asp | His | Val | Ser | Val | Arg | Thr | Leu | |
| | | 480 | | | | 485 | | | | | 490 | | | | | |
| TGA | GGGTCGCGGG | TCGCCGGGGT | CTTGAGGCCG | GAGGGCCTCG | CGTATGCAGT | | | | | | | | | | | 1841 |
| * | | | | | | | | | | | | | | | | |
| GATTCGTGGA | TCACCGGCCA | GTT | | | | | | | | | | | | | | 1864 |

(2) INFORMATION FOR SEQ ID NO:7:

(i) SEQUENCE CHARACTERISTICS:
        (A) LENGTH: 493 amino acids
        (B) TYPE: amino acid
        (D) TOPOLOGY: linear (ii) MOLECULE TYPE: protein (xi) SEQUENCE DESCRIPTION: SEQ ID NO:7:

| | | | | | | | | | | | | | | |
|---|---|---|---|---|---|---|---|---|---|---|---|---|---|---|
| Met | Ile | Thr | Arg | Pro | Ile | Ala | His | Thr | Thr | Ala | Gly | Asp | Leu | Gly | Gly |
| 1 | | | | 5 | | | | | 10 | | | | | 15 | |
| Cys | Leu | Glu | Asp | Gly | Leu | Tyr | Val | Phe | Arg | Gly | Val | Pro | Tyr | Ala | Glu |
| | | | 20 | | | | | 25 | | | | | 30 | | |
| Pro | Pro | Val | Gly | Asp | Leu | Arg | Trp | Arg | Ala | Ala | Arg | Pro | His | Ala | Gly |
| | | | 35 | | | | 40 | | | | | 45 | | | |
| Trp | Thr | Gly | Val | Arg | Asp | Ala | Ser | Ala | Tyr | Gly | Pro | Ser | Ala | Pro | Gln |
| | | 50 | | | | | 55 | | | | | 60 | | | |
| Pro | Val | Glu | Pro | Gly | Gly | Ser | Pro | Ile | Leu | Gly | Thr | His | Gly | Asp | Pro |
| 65 | | | | | 70 | | | | | 75 | | | | | 80 |
| Pro | Phe | Asp | Glu | Asp | Cys | Leu | Thr | Leu | Asn | Leu | Trp | Thr | Pro | Asn | Leu |
| | | | | 85 | | | | | 90 | | | | | 95 | |
| Asp | Gly | Gly | Ser | Arg | Pro | Val | Leu | Val | Trp | Ile | His | Gly | Gly | Gly | Leu |
| | | | | 100 | | | | | 105 | | | | | 110 | |
| Leu | Thr | Gly | Ser | Gly | Asn | Leu | Pro | Asn | Tyr | Ala | Thr | Asp | Thr | Phe | Ala |
| | | | 115 | | | | | 120 | | | | | 125 | | |
| Arg | Asp | Gly | Asp | Leu | Val | Gly | Ile | Ser | Ile | Asn | Tyr | Arg | Leu | Gly | Pro |
| | | 130 | | | | | 135 | | | | | 140 | | | |
| Leu | Gly | Phe | Leu | Ala | Gly | Met | Gly | Asp | Glu | Asn | Val | Trp | Leu | Thr | Asp |
| 145 | | | | | 150 | | | | | 155 | | | | | 160 |
| Gln | Val | Glu | Ala | Leu | Arg | Trp | Ile | Ala | Asp | Asn | Val | Ala | Ala | Phe | Gly |
| | | | | 165 | | | | | 170 | | | | | 175 | |
| Gly | Asp | Pro | Asn | Arg | Ile | Thr | Leu | Val | Gly | Gln | Ser | Gly | Gly | Ala | Tyr |
| | | | 180 | | | | | 185 | | | | | 190 | | |
| Ser | Ile | Ala | Ala | Leu | Ala | Gln | His | Pro | Val | Ala | Arg | Gln | Leu | Phe | His |
| | | 195 | | | | | 200 | | | | | 205 | | | |
| Arg | Ala | Ile | Leu | Gln | Ser | Pro | Pro | Phe | Gly | Met | Gln | Pro | His | Thr | Val |
| | 210 | | | | | 215 | | | | | 220 | | | | |

| Glu | Glu | Ser | Thr | Ala | Arg | Thr | Lys | Ala | Leu | Ala | Arg | His | Leu | Gly | His |
| 225 | | | | | 230 | | | | | 235 | | | | | 240 |

| Asp | Asp | Ile | Glu | Ala | Leu | Arg | His | Glu | Pro | Trp | Glu | Arg | Leu | Ile | Gln |
| | | | | 245 | | | | | 250 | | | | | 255 | |

| Gly | Thr | Ile | Gly | Val | Leu | Met | Glu | His | Thr | Lys | Phe | Gly | Glu | Trp | Pro |
| | | | 260 | | | | | 265 | | | | | 270 | | |

| Leu | Ala | Phe | Tyr | Pro | Val | Phe | Asp | Glu | Ala | Thr | Ile | Pro | Arg | His | Pro |
| | | 275 | | | | | 280 | | | | | 285 | | | |

| Ile | Glu | Ser | Ile | Ile | Asp | Ser | Asp | Ile | Glu | Ile | Ile | Ile | Gly | Trp | Thr |
| | 290 | | | | | 295 | | | | | 300 | | | | |

| Arg | Asp | Glu | Gly | Thr | Phe | Pro | Phe | Ala | Phe | Asp | Pro | Gln | Val | Ser | Gln |
| 305 | | | | | 310 | | | | | 315 | | | | | 320 |

| Ala | Asp | Arg | Asp | Gln | Val | Glu | Ser | Trp | Leu | Gln | Lys | Arg | Phe | Gly | Asp |
| | | | | 325 | | | | | 330 | | | | | 335 | |

| His | Ala | Ala | Ser | Ala | Tyr | Glu | Ala | His | Ala | Gly | Asp | Gly | Thr | Ser | Pro |
| | | | 340 | | | | | 345 | | | | | 350 | | |

| Trp | Thr | Val | Ile | Ala | Asn | Val | Val | Gly | Asp | Glu | Leu | Phe | His | Ser | Ala |
| | | 355 | | | | | 360 | | | | | 365 | | | |

| Gly | Tyr | Arg | Val | Ala | Asp | Glu | Arg | Ala | Thr | Arg | Arg | Pro | Val | Arg | Ala |
| | 370 | | | | | 375 | | | | | 380 | | | | |

| Tyr | Gln | Phe | Asp | Val | Val | Ser | Pro | Leu | Ser | Asp | Gly | Ala | Leu | Gly | Ala |
| 385 | | | | | 390 | | | | | 395 | | | | | 400 |

| Val | His | Cys | Ile | Glu | Met | Pro | Phe | Thr | Phe | Ala | Asn | Leu | Asp | Arg | Trp |
| | | | | 405 | | | | | 410 | | | | | 415 | |

| Thr | Gly | Lys | Pro | Phe | Val | Asp | Gly | Leu | Asp | Pro | Asp | Val | Val | Ala | Arg |
| | | | 420 | | | | | 425 | | | | | 430 | | |

| Val | Thr | Asn | Val | Leu | His | Gln | Ala | Trp | Ile | Ala | Phe | Val | Arg | Thr | Gly |
| | | 435 | | | | | 440 | | | | | 445 | | | |

| Asp | Pro | Thr | His | Asp | Gln | Leu | Pro | Val | Trp | Pro | Thr | Phe | Arg | Ala | Asp |
| | 450 | | | | | 455 | | | | | 460 | | | | |

| Asp | Pro | Ala | Val | Leu | Val | Val | Gly | Asp | Glu | Gly | Ala | Glu | Val | Ala | Arg |
| 465 | | | | | 470 | | | | | 475 | | | | | 480 |

| Asp | Leu | Ala | Arg | Pro | Asp | His | Val | Ser | Val | Arg | Thr | Leu | | | |
| | | | | 485 | | | | | 490 | | | | | | |

( 2 ) INFORMATION FOR SEQ ID NO:8:

( i ) SEQUENCE CHARACTERISTICS:
        ( A ) LENGTH: 51 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Arthrobacter oxidans
        ( B ) STRAIN: P52

( x i ) SEQUENCE DESCRIPTION: SEQ ID NO:8:

CTAGAGATCT    CAACAATGGT    TACCAGACCG    ATCGCCCACA    CCACCGCTGG    G        51

( 2 ) INFORMATION FOR SEQ ID NO:9:

( i ) SEQUENCE CHARACTERISTICS:
        ( A ) LENGTH: 49 base pairs
        ( B ) TYPE: nucleic acid ( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:9:

GTCCCCAGCG GTGGTGTGGG CGATCGGTCT GGTAACCATT GTTGAGATC 49